(12) United States Patent
Virr et al.

(10) Patent No.: US 9,248,248 B2
(45) Date of Patent: Feb. 2, 2016

(54) RESPIRATOR

(75) Inventors: Alexander Virr, Mangrove Mountain (AU); Dan Kao, Northbridge (AU); Xiaoyi Fu, Epping (AU); John Michael Snow, Killarney Heights (AU); Junning Chen, Carlingford (AU)

(73) Assignee: PAFTEC TECHNOLOGIES PTY LTD, St. Leonards (AU)

( * ) Notice: Subject to any disclaimer, the term of this patent is extended or adjusted under 35 U.S.C. 154(b) by 738 days.

(21) Appl. No.: 13/384,577

(22) PCT Filed: Jul. 15, 2010

(86) PCT No.: PCT/AU2010/000902
§ 371 (c)(1),
(2), (4) Date: Mar. 30, 2012

(87) PCT Pub. No.: WO2011/006206
PCT Pub. Date: Jan. 20, 2011

(65) Prior Publication Data
US 2012/0174922 A1    Jul. 12, 2012

(30) Foreign Application Priority Data

Jul. 17, 2009    (AU) ................ 2009903362

(51) Int. Cl.
*A62B 17/04*    (2006.01)
*A62B 18/00*    (2006.01)
(Continued)

(52) U.S. Cl.
CPC ......... *A61M 16/0066* (2013.01); *A61M 16/105* (2013.01); *A62B 18/025* (2013.01);
(Continued)

(58) Field of Classification Search
CPC ............ A61M 16/066; A61M 16/105; A61M 16/1065; A61M 2016/0661; A62B 18/084; A62B 18/025
USPC .............. 128/201.22, 201.23, 201.28, 201.29
See application file for complete search history.

(56) References Cited

U.S. PATENT DOCUMENTS 4,103,197 A  *  7/1978  Ikegami et al. ................ 310/267
4,462,399 A     7/1984  Braun ....................... 128/201.25
(Continued)

FOREIGN PATENT DOCUMENTS

CN    101034840 A    9/2007
EP    0621056        10/1994
(Continued)

OTHER PUBLICATIONS

Examination Report from the New Zealand Intellectual Property Office for Patent Application No. 598037, dated Oct. 15, 2012.
(Continued)

*Primary Examiner* — Justine Yu
*Assistant Examiner* — Kathrynn Lyddane
(74) *Attorney, Agent, or Firm* — Ballard Spahr LLP

(57) ABSTRACT

A breathing apparatus, including a mask and a neck component. The mask is adapted to substantially surround at least the mouth or nostrils of a user. The neck component is attached to said mask, and adapted to substantially surround the back of the neck of said user. The neck component includes a flow generator to receive unfiltered air from a surrounding environment, filter said unfiltered air, and, provide filtered air to said mask. The breathing apparatus has a 'low profile' appearance and is adapted to sit comfortably about the neck of the user.

13 Claims, 30 Drawing Sheets

(51) Int. Cl.
  *A61M 16/00* (2006.01)
  *A61M 16/10* (2006.01)
  *A62B 18/02* (2006.01)
  *A62B 18/08* (2006.01)

(52) U.S. Cl.
  CPC ...... *A62B18/084* (2013.01); *A61M 2016/0039* (2013.01); *A61M 2205/3368* (2013.01); *A61M 2205/3606* (2013.01); *A61M 2205/3653* (2013.01); *A61M 2205/3673* (2013.01)

(56) References Cited

U.S. PATENT DOCUMENTS

| | | | |
|---|---|---|---|
| 4,671,268 A | 6/1987 | Hunt | 128/201.13 |
| 4,671,269 A * | 6/1987 | Wilp | 128/202.25 |
| 4,951,662 A * | 8/1990 | Townsend, Jr. | 128/205.25 |
| 6,550,479 B1 * | 4/2003 | Duxbury | 128/205.27 |
| 6,953,318 B2 * | 10/2005 | Krugerke | 415/26 |
| 6,971,386 B2 | 12/2005 | Duxbury | 128/200.24 |
| 7,195,014 B2 * | 3/2007 | Hoffman | 128/204.18 |
| 7,392,806 B2 * | 7/2008 | Yuen et al. | 128/205.27 |
| 7,481,220 B2 * | 1/2009 | Meyer et al. | 128/207.11 |
| 2003/0154983 A1 | 8/2003 | Marx | 128/206.12 |
| 2005/0284481 A1 | 12/2005 | Meyer | 128/207 |
| 2007/0210657 A1 | 9/2007 | Chen | 310/67 R |
| 2007/0240716 A1 | 10/2007 | Marx | 128/206.12 |
| 2007/0251527 A1 * | 11/2007 | Sleeper | 128/204.21 |
| 2008/0047558 A1 | 2/2008 | Duxbury | 128/205.24 |
| 2009/0145429 A1 | 6/2009 | Ging et al. | |
| 2009/0188085 A1 * | 7/2009 | Serbu et al. | 24/20 S |
| 2010/0059056 A1 * | 3/2010 | Sears et al. | 128/204.18 |
| 2010/0170513 A1 * | 7/2010 | Bowditch et al. | 128/204.23 |

FOREIGN PATENT DOCUMENTS

| | | |
|---|---|---|
| FR | 2872051 | 12/2005 |
| GB | 2201895 | 9/1988 |
| JP | 3022363 U | 3/1996 |
| JP | 2000-23395 A | 1/2000 |
| JP | 2000-234213 | 8/2000 |
| JP | 2004000574 A | 1/2004 |
| JP | 2007-151823 A | 6/2007 |
| JP | 2008264457 A | 11/2008 |
| JP | 2010-512198 | 8/2010 |
| WO | WO-2005004974 A1 | 1/2005 |
| WO | WO-2008011682 A1 | 1/2008 |
| WO | WO 2011/006206 | 1/2011 |

OTHER PUBLICATIONS

Amendments filed Jul. 7, 2011 to the European Patent Office for Application No. 10799289 filed Jul. 25, 2010 (Applicant—PAFtec Technologies Pty. Ltd. // Inventor—Virr, et al.) (pp. 1-43).

International Preliminary Report on Patentability issued Nov. 17, 2011 by the International Searching Authority for Application No. PCT/AU2010/000902 filed Jul. 15, 2010 (Applicant—PAFtec Technologies Pty. Ltd. // Inventor—Virr, et al.) (pp. 1-8).

International Search Report issued Sep. 29, 2010 by the International Searching Authority for Application No. PCT/AU2010/000902 filed Jul. 15, 2010 (Applicant—PAFtec Technologies Pty. Ltd. // Inventor—Virr, et al.) (pp. 1-5).

Written Opinion issued Sep. 29, 2010 by the International Searching Authority for Application No. PCT/AU2010/000902 filed Jul. 15, 2010 (Applicant—PAFtec Technologies Pty. Ltd. // Inventor—Virr, et al.) (pp. 1-9).

* cited by examiner

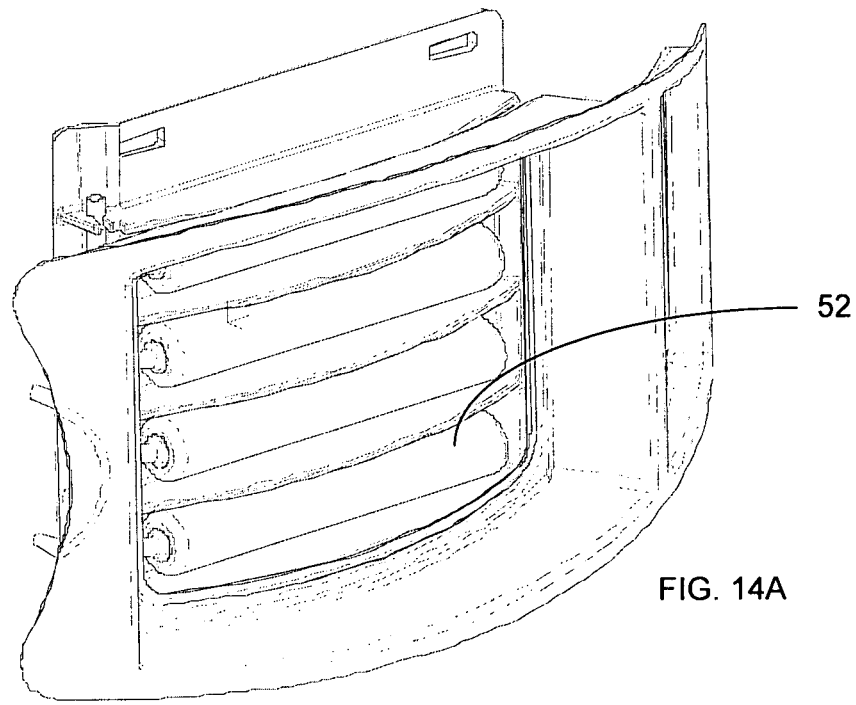
FIG. 14A
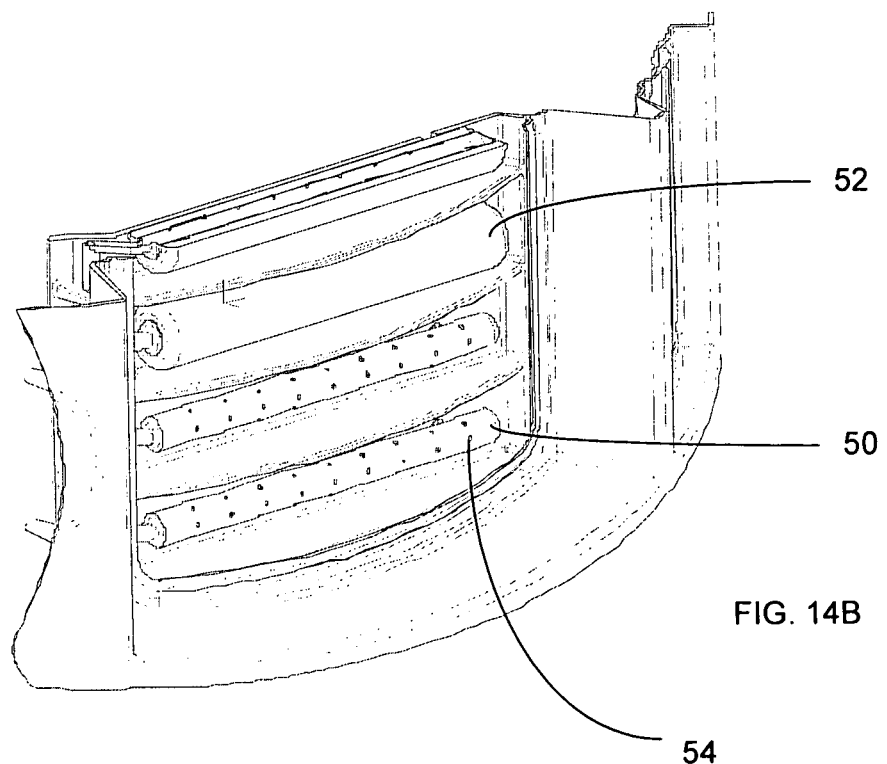
FIG. 14B
FIG. 14

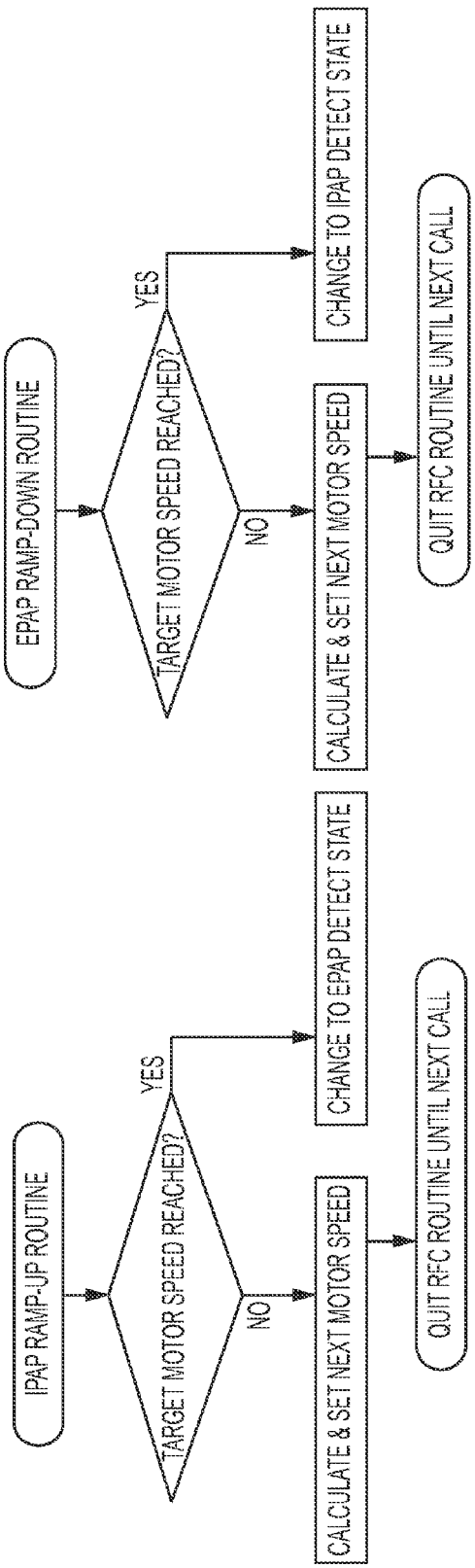

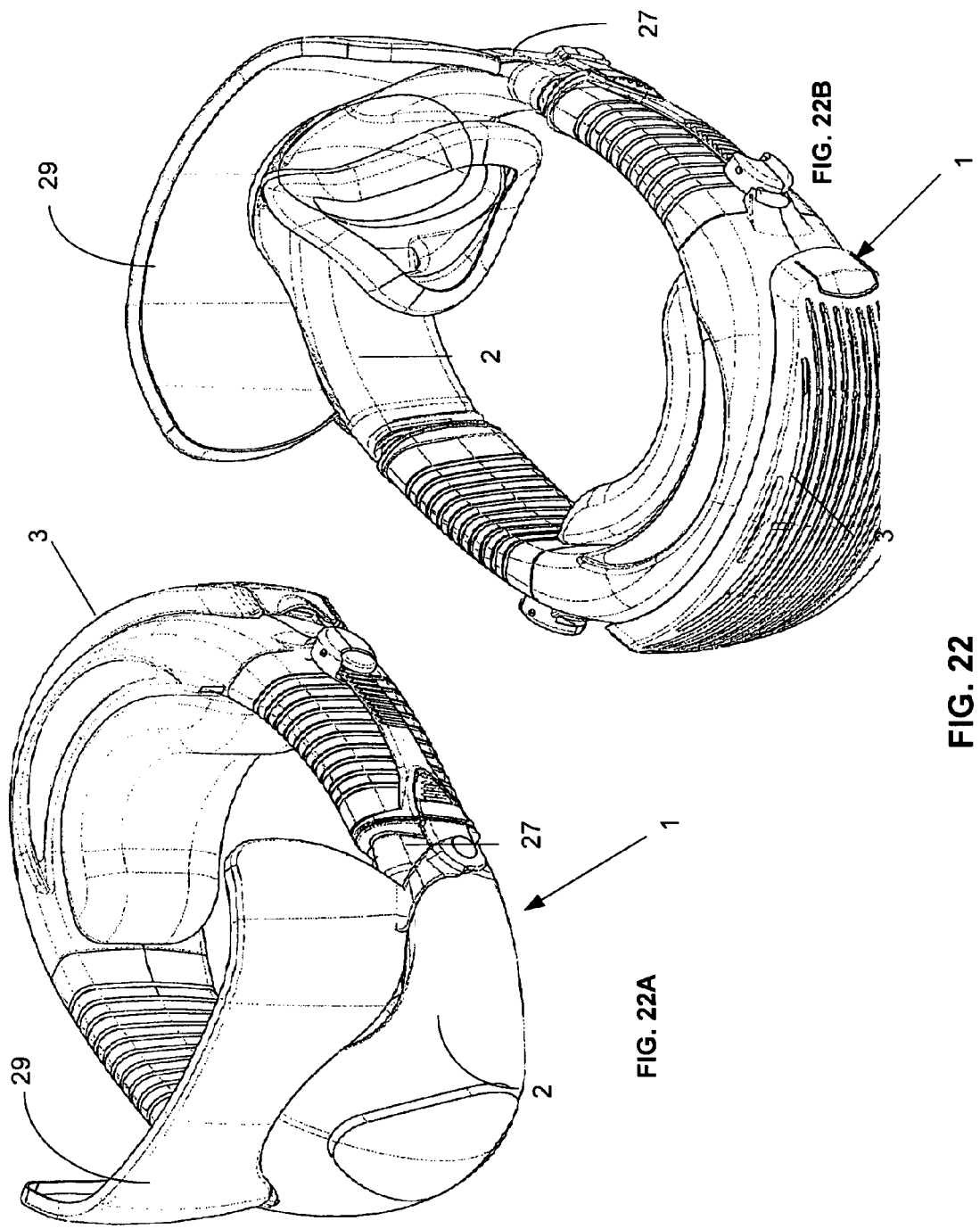

RESPIRATOR

CROSS REFERENCE TO RELATED APPLICATIONS

The present application is a National Phase Application of International Application No. PCT/AU2010/000902, filed Jul. 15, 2010, which claims priority to Australian Patent Applications No. 2009903362, filed Jul. 17, 2009, which applications are incorporated herein fully by this reference.

BACKGROUND OF THE INVENTION

The present invention relates to a breathing apparatus, and in particular to a low profile powered air purifying respirator. The present invention also relates to a respirator mask, and a respirator system which has a low profile design, which is comfortable and easy to wear about the neck of a user, which is aesthetically pleasing due to its compact construction and low profile appearance, and, which is effective and efficient to operate in a variety of applications, including everyday applications, on worksites and industrial situations.

DESCRIPTION OF THE PRIOR ART

The reference in this specification to any prior publication (or information derived from it), or to any matter which is known, is not, and should not be taken as, an acknowledgement or admission or any form of suggestion that that prior publication (or information derived from it) or known matter forms part of the common general knowledge in the field of endeavour to which this specification relates.

A powered air purifying respirator, or PAPR, typically uses power to draw ambient air from the atmosphere through a filter element, to pressurize it, and transfer it to the airways of the user via a conduit and mask. A PAPR ensures that the supply of air remains filtered or purified under all circumstances by maintaining a positive pressure inside the mask. PAPR devices are currently used where the environment is heavily polluted or hazardous, to supply purified air to a user. Such environments traditionally include polluted industrial areas, or hospitals.

All currently known PAPR systems are specified solely for professional and industrial applications. That is, they have not been designed for use by the general public in everyday situations. Therefore, the size of most PAPR systems is typically big & heavy. Some known PAPR systems have filtering capability relocated to the hardhat/or helmet (U.S. Pat. No. 4,462,399), but this attempt does not improve compactness, nor encourage a lightweight structure, but rather, makes the device bulky and top-heavy for users' heads. Some known PAPR systems can be carried as a backpack, encased in elastic bag with shoulder straps to carry the device, however, this is as portable as the device could be, and does not allow for other carrying methods when the strap/bag configuration is not used. As a result, most existing PAPR systems would not encourage users to use these systems other than when it is really necessary, that is, in toxic or hazardous areas which occur in industrial environments.

For the general public, protection from pollution and disease in their daily life relies largely on dust or surgical marks. However, these masks only provide basic protection, due to leakage around the masks, even when the filter material used in making such masks is typically labeled as suitable for high efficiency filtering. Due to the extra resistance imposed by the filter media, the user has to breathe considerably harder than they normally do without the mask. Thus, it is quite difficult for anyone to use such a mask comfortably for a prolonged period. Furthermore, $CO_2$ and moisture accumulate inside the mask, which tends to make the situation worse. In addition, the higher the efficiency of the filter media, the higher the flow resistance it will impose, thus making these masks even more uncomfortable for prolonged use. Such effects are particularly obvious for those who have weak or impaired respiratory systems, such as elderly people, children, and the sick, such as asthma and COPD patients.

Dust and surgical masks have therefore been widely used by general public largely because of their ease of use and the fact that there are not any acceptable PAPR solutions available should anyone wish to use a more efficient and comfortable device.

However, it is apparent that the air quality in many everyday situations can be very poor. In larger cities, the heavy density of cars, buses, trucks and motorcycles often emit excessive amounts of toxic pollutants. Power plants are another key source of pollutions. Natural or man-made disasters, such as sandstorms, fires of any kinds, also contribute harm to people's respiratory systems. Those pollutions include dust (suspended particles), lead, and harmful gases such as $NO_2$, $SO_2$, CO, $O_3$, VOCs, smoke, etc. Long term exposure to these pollutions is evidenced to be harmful and often causes life threatening diseases. SARS, bird and swine influenza, three of the most recent disease-related threats to humans are also pollutants, or air borne diseases, and are potentially deadly to human beings.

A protection device that offers the similar level of protection and comfort to PAPR and yet can also be acceptable to use by ordinary people or light industrial/professional users is clearly needed.

SUMMARY OF THE INVENTION

The present invention seeks to overcome the deficiencies of the prior art.

The present invention also seeks to provide a low-profile respirator.

Throughout this specification, the term 'low profile' is used. This term is intended to refer to a mask which, whilst covering the nose and/or mouth of the user similar to that of a 'dust mask', is relatively small and compact in size and shape, such that it is relatively aesthetically pleasing in appearance when worn, particularly compared with the traditional bulky and heavy industrial masks of known powered respirators. Such prior art powered respirators used in industrial applications appear cumbersome and typically have air tubes supplying the air into the mask chamber provided on the front of the masks, rendering those masks particularly aesthetically unappealing.

The present invention also seeks to provide a respirator which includes one or more of the advantages of being easy to carry, easy to don and doff, having improved perception/image while in use, and, which is cost effective.

The present invention also seeks to provide a low profile respirator which can function as a pollution protection device, or as a breathing assistance or breathing therapy apparatus.

Typical examples of people in domestic environments who may benefit from such a said device include daily commuters; motorcyclists, electric bicycle riders, passengers, pedestrians and road workers, traffic officers, road repairers, construction workers, airport staffs, clean room/laboratory workers, food processing workers, poultry farmers, those working in hospitals treating and containing outbreaks, schools, smoke zone workers, etc.

In one broad form, the present invention provides a breathing apparatus, including: a mask, adapted to substantially surround at least the mouth or nostrils of a user; and a neck component, attached to said mask, adapted to substantially surround the back of the neck of said user, said neck component including a flow generator to receive unfiltered air from a surrounding environment, filter said unfiltered air, and, provide filtered air to said mask.

Preferably, said neck component is attached to said mask by at least one engagement arrangement.

Preferably, each said engagement arrangement includes: at least one cooperating air channel on said mask and said neck component; at least one cooperating mating clip to releasably mate said mask and said neck component together.

Also preferably, each air channel is at least partly formed of an elastomeric material.

Also preferably each mating clip includes a ratchet.

Preferably at least a seal portion of said mask is at least partly formed of silicone rubber or the like.

Preferably said filtered air is transferred between said neck component and said mask via integrally formed air channels.

Also preferably, all componentry for operation of said breathing apparatus are housed within said neck component.

Preferably, said neck component further includes any one or combination of:
 a flow sensor;
 a pressure sensor;
 a negative ion generator;
 a heater;
 a cooler;
 a filter assembly;
 a blower;
 a power supply;
 a muffler;
 a user interface; and,
 a humidifier/dehumidifier.

Preferably the present invention further includes a cover, to decorate said mask, including fabric or other material, and/or a visor to provide protection to the eyes of said user.

Also preferably the present invention further includes a strap or band, adapted to be attached over the head of a user, to retain said mask in position.

Preferably said flow sensor and/or said pressure sensor is adapted to provide a feedback signal to said flow generator to adjust said air flow and/or air pressure of said mask, that is, be breath responsive, said breath responsiveness of said flow/pressure sensor being optionally user adjustable.

Also preferably, said filter assembly further includes any one or combination of:
 a coarse filter;
 a pre-filter;
 a high efficiency particulate air (HEPA) filter;
 an advanced carbon filter;
 an activated carbon filter (steam activated or multiple chemical activated);
 a photo catalyst filter or coating (ambient light and/or LED activated); and,
 a cold catalyst filter.

Preferably said neck component further includes control means, said control means including any one or combination of:
 a user controlled interface;
 a remote controller;
 a rechargeable battery;
 a battery pack; and
 a motor controller.

Also preferably said apparatus is manufactured to have a 'low profile' appearance, and which is adapted to sit comfortably about the neck of said user, optionally including padded portions.

Preferably, said breathing apparatus includes: a sensor, to sense the temperature and/or humidity of said air; a comparator, to compare said sensed temperature and/or humidity with a predetermined value; and, climate control means including at least one of a heater, cooler, humidifier and dehumidifier, to provide any necessary adjustment of temperature and/or humidity of said filtered air provided to said mask to said predetermined value.

Also preferably, said predetermined value is either preset by a manufacturer or is user adjustable.

Preferably, said breathing apparatus includes a negative ion generator having a control to operate in sync with a users' breathing pattern (on with inhalation and off with exhalation).

Preferably, said breathing apparatus includes a brushless DC motor having a stator with a toroidal core, characterised in that said core includes a plurality of radial fins extending inwardly therefrom to form a divide between respective coils formed therebetween.

Also preferably, said radial fins are formed either by integrally moulding with the core, or, by overmoulding the core.

Preferably, said breathing apparatus further includes an exhaled air filter, to filter air exhaled by said user before being egressed to the surrounding environment.

Also preferably, said exhaled air filter is integrally formed with an exhaust valve of said breathing apparatus.

In a further broad form, the present invention provides a mask, adapted to substantially surround at least the mouth or nostrils of a user; and, a climate control means, including at least one of a heater, cooler, humidifier and dehumidifier, to adjust the temperature and/or humidity of said air provided to said user.

Preferably, the breathing apparatus further includes a filter to receive unfiltered air from a surrounding environment and provide filtered air to said mask.

In a further broad form, the present invention provides a mask, adapted to substantially surround at least the mouth or nostrils of a user; and, a negative ion generator having control to operate in sync with a user's breathing pattern (on with inhalation and off with exhalation).

In yet a further broad form, the present invention provides a mask, adapted to substantially surround at least the mouth or nostrils of a user; and an exhaled air filter to filter air exhaled by a user before being egressed to a surrounding environment.

Preferably, said exhaled air filter is integrally formed with an exhaust valve of said breathing apparatus.

In a further broad form, the present invention provides a brushless DC motor having a stator with a toroidal core including a plurality of radial fins extending inwardly from said core to form a divide between respective coils, wherein said radial fins are formed either by integrally moulding with the core, or by overmoulding the core.

BRIEF DESCRIPTION OF THE DRAWINGS

The present invention will become more fully understood from the following detailed description of preferred but non limiting embodiments thereof, described in connection with the accompanying drawings, wherein:

FIG. 14 illustrates a different design of wicking fingers;

FIG. 22 shows an alternative version of the invention, including a visor.

DETAILED DESCRIPTIONS OF THE PREFERRED EMBODIMENTS

Throughout the drawings, like numerals will be used to identify similar features, except where expressly otherwise indicated.

Respirator Mask Assembly

The respirator or breathing apparatus assembly of the present invention, includes a mask component and a neck component. The mask component is adapted to substantially surround the mouth and/or neck of the user, whilst the neck component is attachable thereto and is adapted to surround the back of the neck of the user. The neck component includes the flow generator and associated processing means to receive in filtered air from the surrounding environment, filter the unfiltered air and provide the filtered air to the mask.

Figure 1:
FIG. 1 shows a person wearing a breathing apparatus in accordance with the present invention.

FIG. 1 illustrates a person wearing a breathing apparatus in accordance with a preferred form of the present invention. As illustrated, the apparatus 1 is of considerably improved aesthetically pleasing visual appearance, and is relatively low profile compared with prior art respiratory devices. The mask is relatively comfortably worn covering at least the mouth or nose of the user, and extending around the neck of user. All componentry in the breathing apparatus, may be wholly contained within this face and neck assembly.

Figure 2:
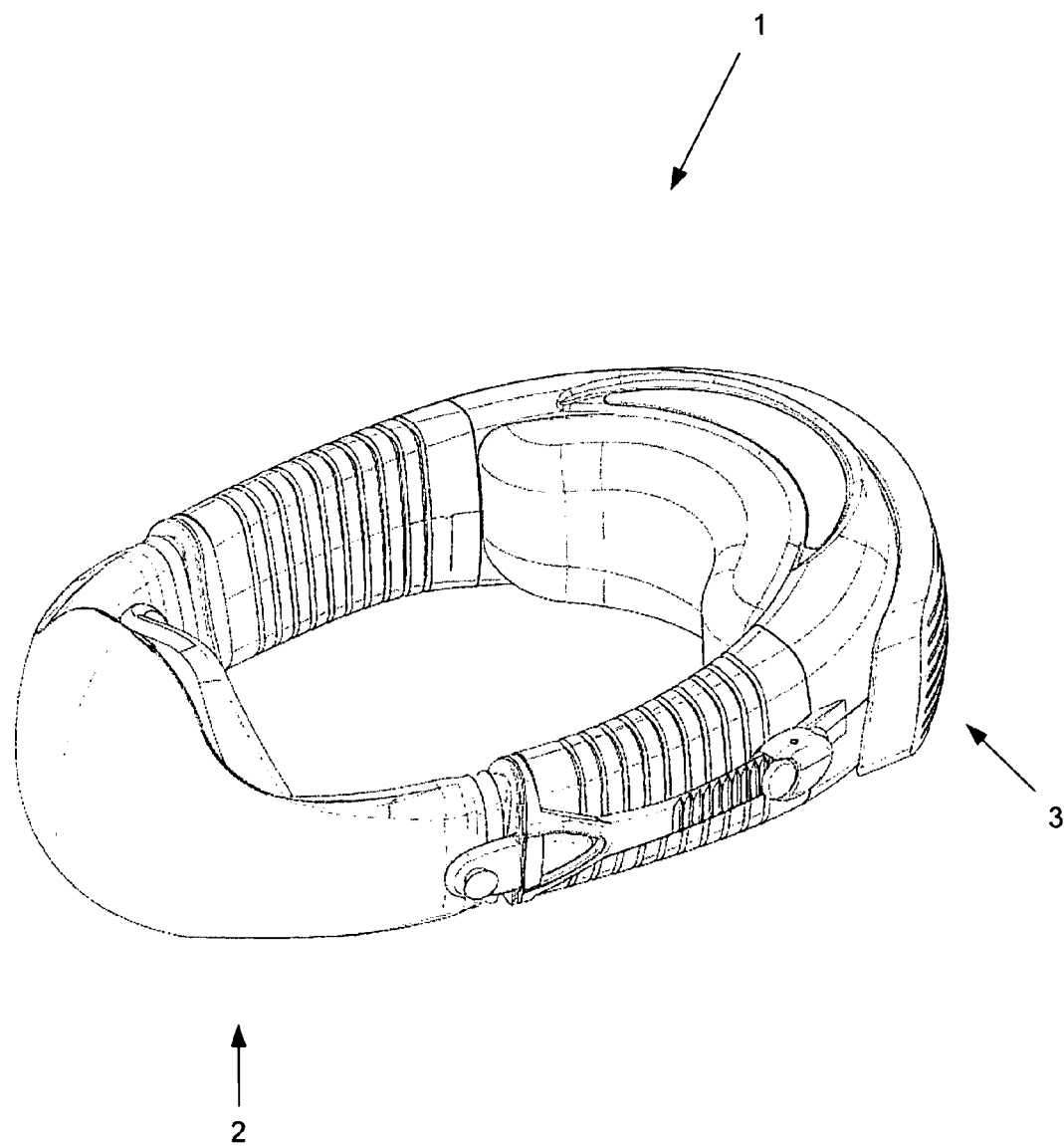
FIG. 2 shows a perspective view of the breathing apparatus.

FIG. 2 illustrates a perspective view of the breathing apparatus 1, including a mask component 2 and a neck component 3, which are at least partly detachable from each other.

Figure 3:
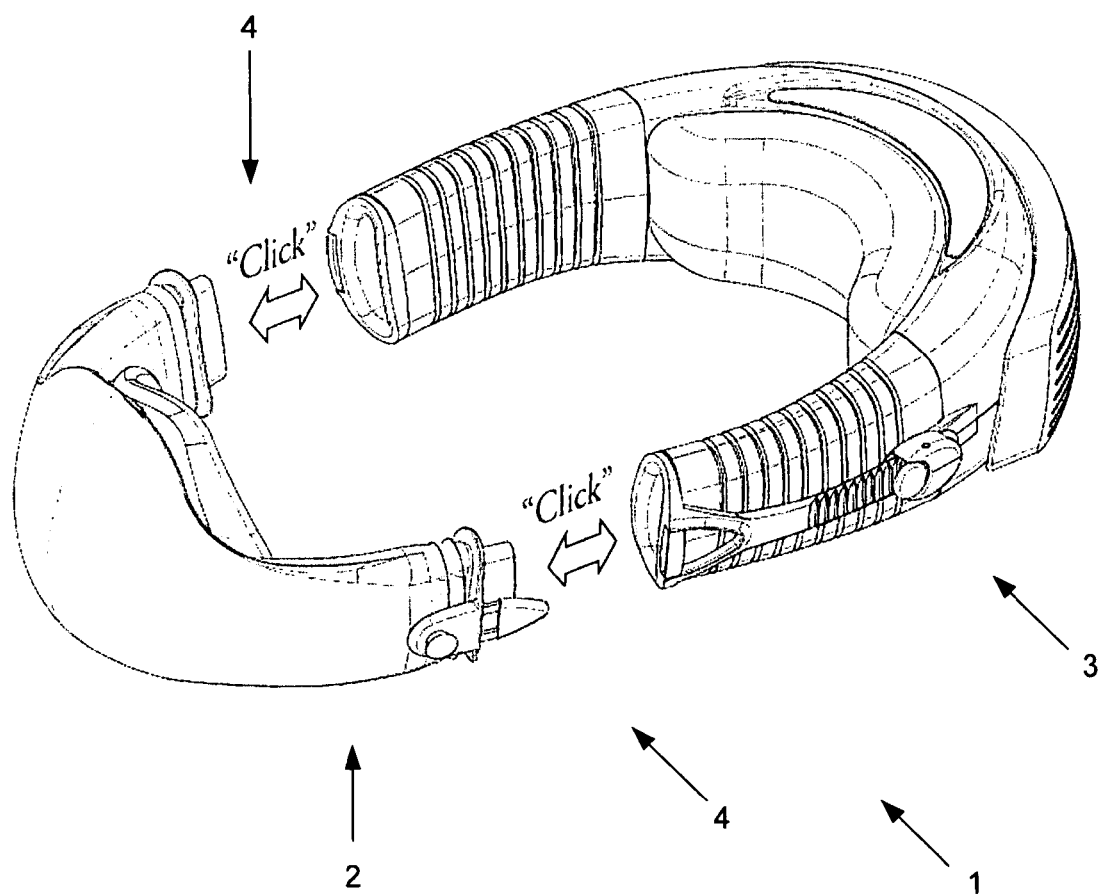
FIG. 3 shows an exploded perspective view of the breathing apparatus of FIG. 2.

FIG. 3 illustrates an exploded view of the breathing apparatus 1, showing the mask component 2 separated from the neck component 3. This is achieved by an appropriate cooperating engagement means 4 provided on the mask 2 and neck component 3 to engageably attach the assembly together.

Figures 4, 4A, 4B:
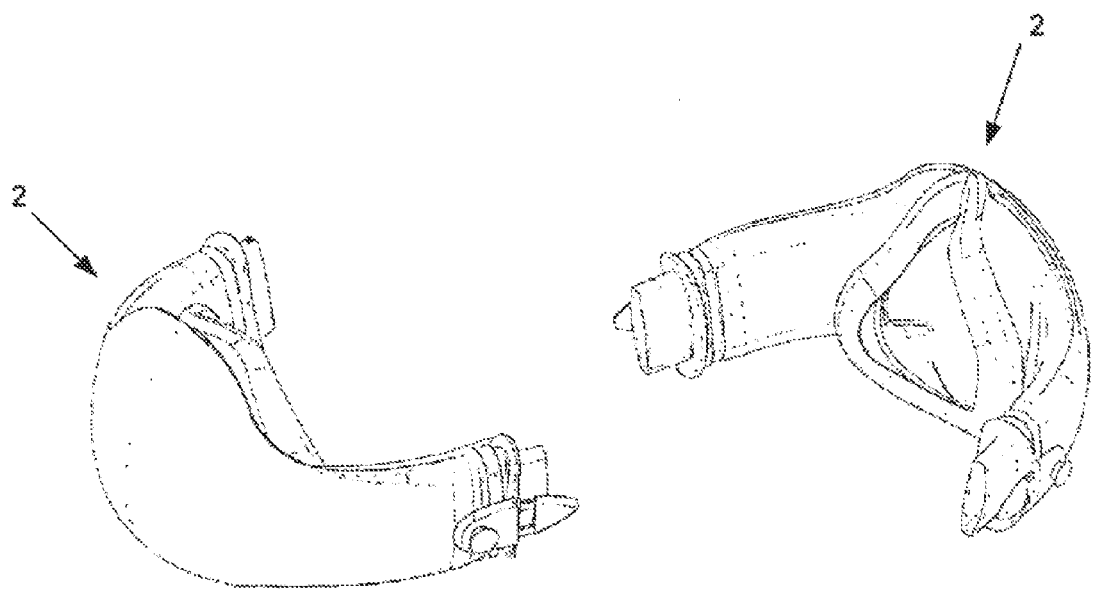
FIG. 4 shows, in FIGS. 4A and 4B respectively, front and rear perspective views of the mask component of the breathing apparatus.

FIG. 4 illustrates, in FIGS. 4A and 4B, front perspective and rear perspective views of the mask component 2, respectively.

Figure 5:
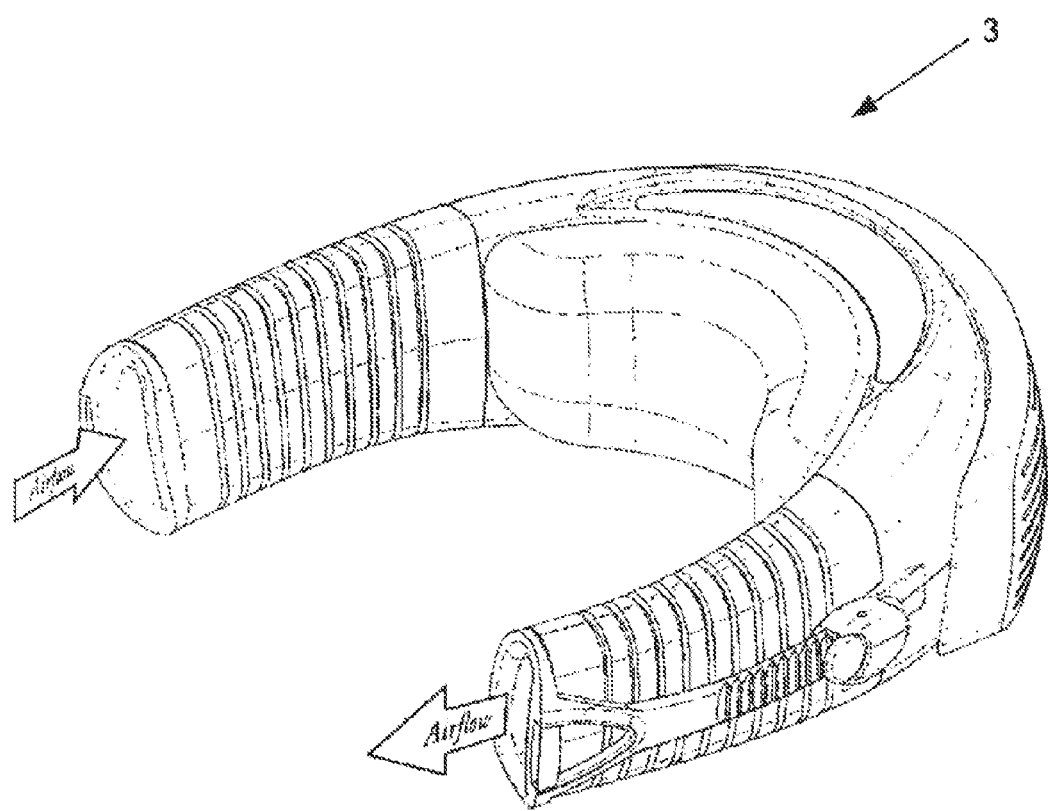
FIG. 5 shows a perspective view of the neck component of the breathing apparatus which incorporates the flow generator.

FIG. 5 illustrates a perspective view of the neck component 3 which is attachable to the mask component 2 of FIG. 4.

Referring to FIGS. 1 to 5, it can be seen that the mask component 2 is adapted to surround the oronasal area, that is, the mouth, nostrils or nose of a user. Alternative embodiments may cover either one of the mouth or nose, having an even lower 'low profile' appearance.

At least part of the mask component 2 may preferably be formed of a suitable material, to provide a good seal between the face and the air paths of the mask 2, whereby leakage of air/gas is substantially avoided, to effectively provide an airtight seal by sealingly contacting and "cushioning" the face of the user. The mask components may typically be made of plastics or rubber materials, such as rubber or silicone. The mask component 2, when formed of such material, may then be washed or sterilised, as required.

A cover may be optionally provided to decorate the mask. The cover may be formed of fabric or other material. An in-mould decoration may be alternatively or additionally provided to the mask.

Figure 6:
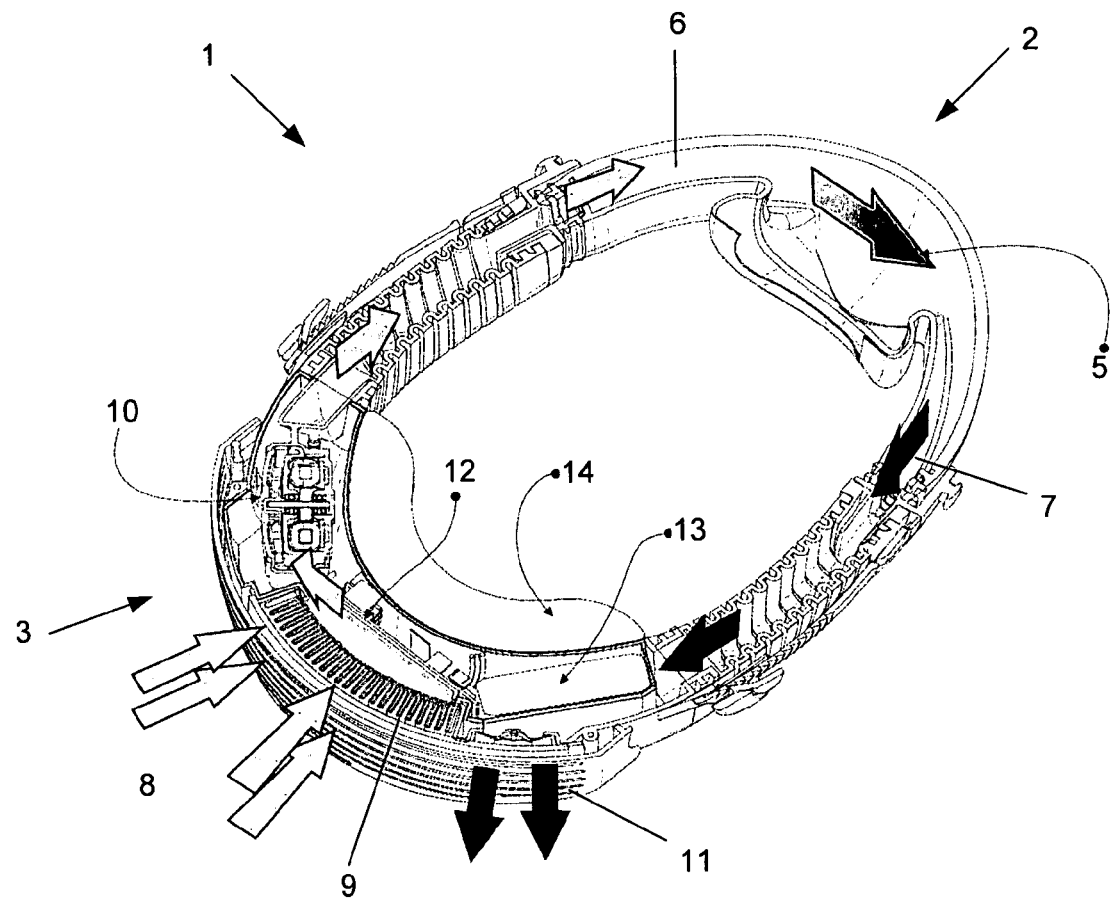
FIG. 6 shows a sectional view of the breathing apparatus, showing the air paths.

As shown in FIG. 6, a breathing chamber 5 is provided in the space between the face of the user and the shell of the mask 2. The breathing chamber 5 is effectively isolated from the surrounding environment by virtue of a seal about the face of the user. One or more air channels, ducts, or conduits 6 and 7 may be provided to connect the breathing chamber 5 with the other parts of the breathing apparatus. In the embodiment shown in FIG. 6, there is provided, in the mask 2, an air inlet 6 and an air outlet 7, for this purpose.

When the mask 2 is attached to the neck component 3, continuous air channels are therefore provided between the two components. The means for attachment of these two components will be described hereinafter.

The neck component 3 of FIG. 5, is adapted to be attached to the mask 2, and in use, is adapted to substantially surround the back of the neck of the user. The neck component 3 includes the flow generator means for generating the flow of air to and from the mask component 2, taking unfiltered air from the surrounding environment through an air intake means 8, filtering the unfiltered air via a filter 9, and effecting a flow of air by a motor or impellor 10, through the air channel 6 to the mask chamber 5. Air exhaled into the mask by the user chamber 5 is then progressed via air channel 7 through outlet 11 to the surrounding environment. The typical flow of air within the breathing apparatus 1 is shown by the arrows in FIG. 6

Appropriate electronic components 12, a battery 13 or the like and other components are all preferably housed within the neck assembly 3. The neck assembly also preferably incorporates a neck pad 14 to provide cushioning for comfort of the user and is also to help maintain the mask seal as the user's head undergoes movement.

Figure 7:
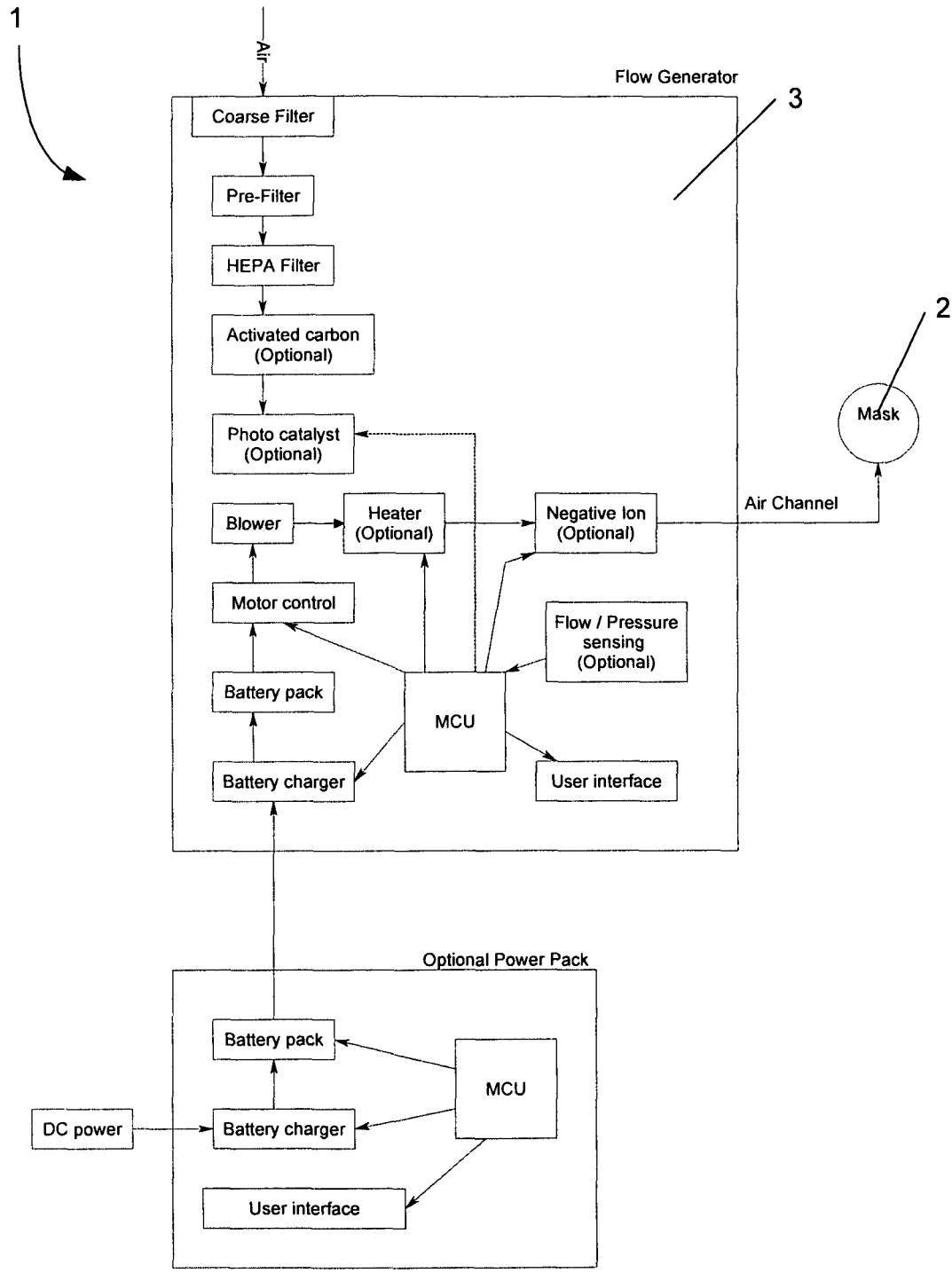
FIG. 7 illustrates the typical component features which may be incorporated in the breathing apparatus of the present invention, and their interrelationship.

In FIG. 7 is shown a block diagram of various component features which may be typically included in the breathing apparatus, showing that most are installed in the neck assembly 3, and, their interrelationship. Also shown is the provision of an optional additional power pack, and the interrelationship of the neck assembly via the air channel to the mask assembly.

Pneumatic Connection and Tension Transmission Clip

Existing PAPR devices use separate means for securing the mask to the face and for supplying air to the mask. For instance, many PAPR use a flexible hose to supply air from the flow generator to the mask, and, a separate head strap to hold the mask on the face. Others mount the fan in an enclosure on top of the user's head and discharge the air directly into the mask, but use a separate strap or band to hold the mask against the face.

In these prior art devices, the user is forced to assemble and release multiple connections every time he or she dons or doffs the device. Also, in those devices where the fan is mounted integrally with the mask, there is a great risk that washing the mask (which is necessary for hygiene) will cause water damage to the fan or control electronics.

Ideally both the air supply to the mask and the tension to keep it in place would be supplied by a single connection between the flow generator and the mask. Ideally also it would be easy to completely disconnect the mask from the flow generator, for cleaning. The present invention achieves both of these objectives with a component that combines the functions of a pneumatic connector with those of a clip (as used on a backpack or other piece of luggage).

Figure 8:
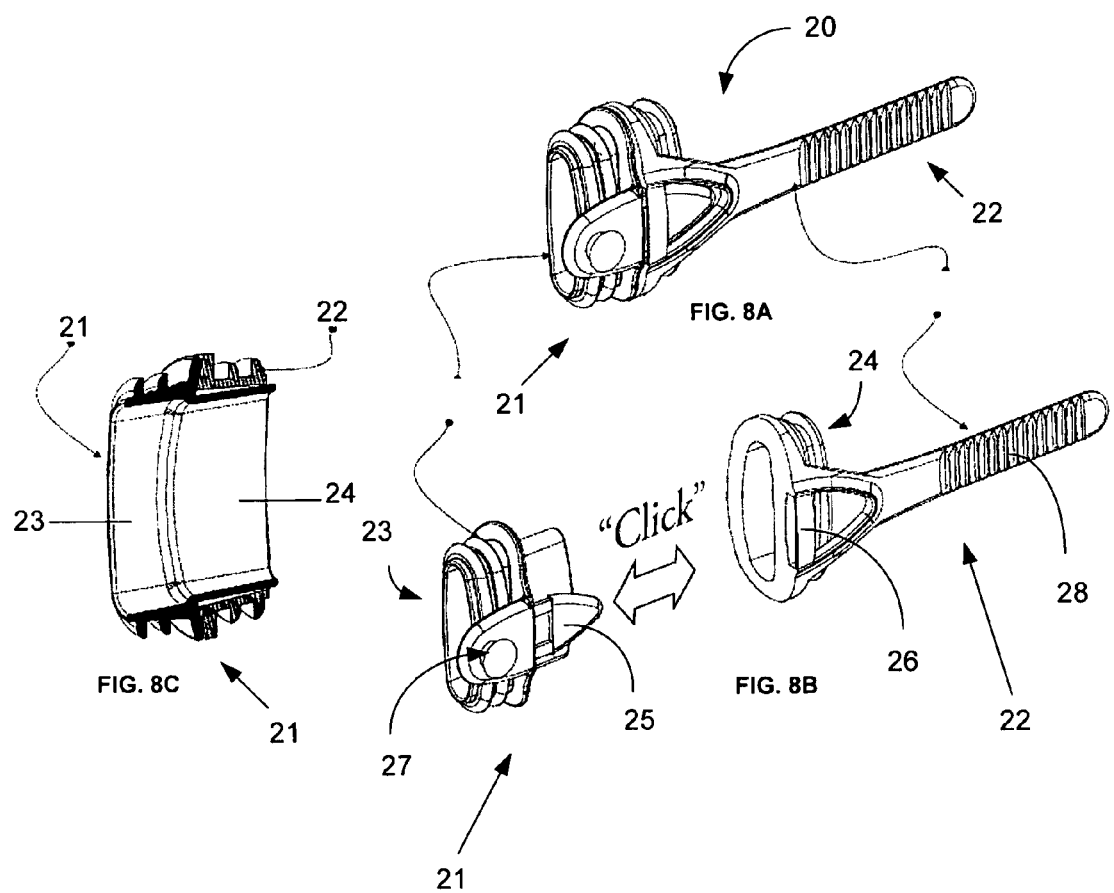
FIG. 8 details the engagement arrangement which may be used to engage the mask and neck component together.
Figure 9:
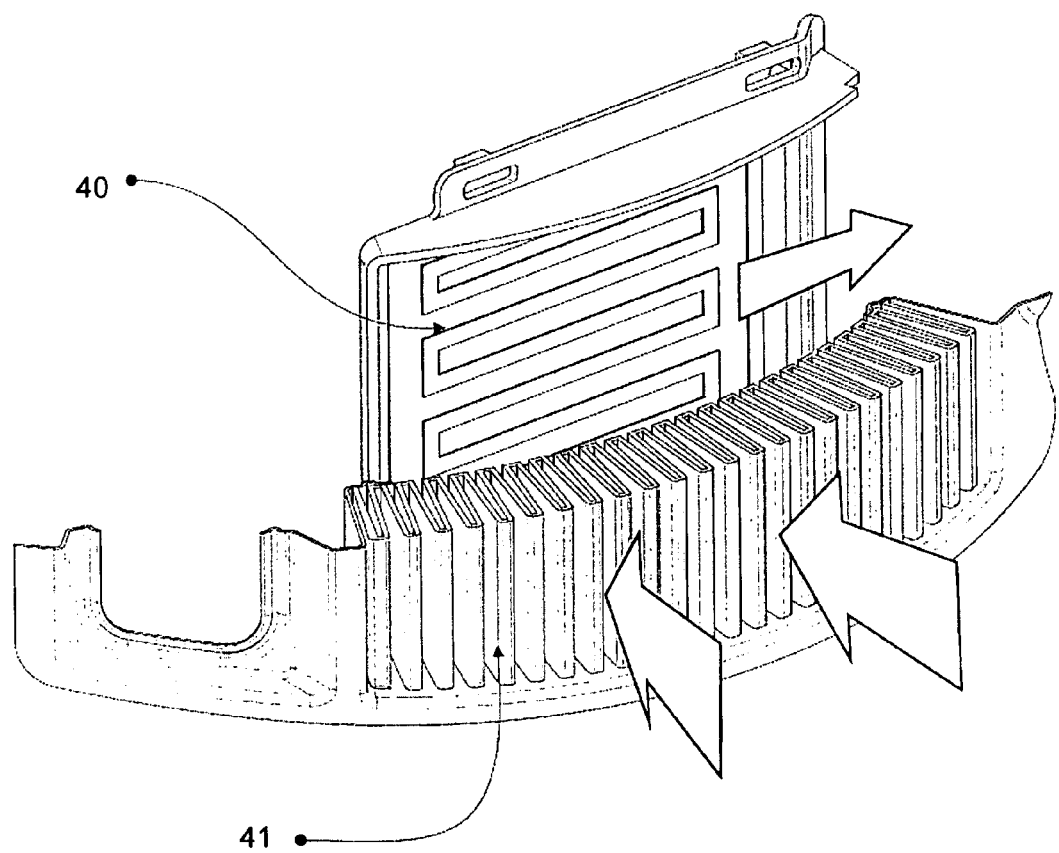
FIG. 9 details a heater which may be installed in the breathing apparatus.

The engagement arrangement, shown in FIG. 8 consists of two components, a mask portion 21 and a neck portion 22, each secured to an elastomeric tube. Each component has a respective air channel 23 and 24, so that air can pass through the clip 20. A seal is formed on one of the elastomeric tubes, so positioned that when the clip is assembled it presses against the opposite clip half. This seal may take the form of a circular cross-section element (like an o-ring) however it is preferably a wiper seal as this design creates less friction when the clip is assembled or dismantled. Alternatively the seal may be a separate component (for instance an o-ring) that is fitted to or over-moulded on one or other clip half.

The two halves of the engagement arrangement 20 are so designed as to provide the ability to transmit tension from one elastomeric tube to the other, but to also be easy to release. For instance they may be provided with one or more beam-like elements with barbs that snap into mating features on the opposite half of the clip. The barbed features take the form of large buttons. Pressing on them disengages the barb(s) and allows the two halves to be separated.

In the preferred embodiment two such engagement arrangements 20 are used, one in the air-supply pipe and one in the air-return pipe. In normal use only one of the clips is disconnected when removing the device from the head. However when mask cleaning is required the other clip can also be opened, so that the flow generator or neck component is entirely separated from the mask.

Single Action Adjustment of the Mask

Existing designs of PAPR rely on either an elastomeric strap or some form of rigid band to maintain tension on the mask and thus seal it against the user's face. Both types of systems can be difficult and slow to adjust and tend to suffer from other problems. In particular, the adjustment mechanisms for such elastomeric straps tend to require considerable force for their adjustment. Rigid systems do not compensate for any change in the distance between the flow generator and the user's face for instance during head movement. For this reason they tend to suffer leaks between the mask cushion and the face.

In FIG. 8, is shown details of an engagement arrangement which may be utilised with the breathing apparatus of the present invention, to engage the neck component and the mask together. The engagement arrangement is shown engaged in FIG. 8A and in exploded view in FIG. 8B. A sectional view is also shown in FIG. 8C. The engagement arrangement 20, includes a mask portion 21 and a neck portion 22, and includes cooperating air channel apparatus 23 and 24, and cooperating mating means 25 and 26 to physically clip the components together in a releasable manner. Additional attachment means 27 may be optionally provided to engage an additional elastomeric strap which may be placed over the head of a user. A ratchet mechanism 28 may also be provided for adjustment of the 'size' of the assembled breathing apparatus, as will be hereinafter described.

FIG. 8C shows a cross-sectional view of the engaged air channel components 23 and 24, illustrating how an air-tight air channel is thereby formed.

The present design overcomes the deficiencies in prior art devices by providing a number of unique features. Firstly, the mounting point is preferably designed to be provided approximately half way between the neck component and the mask. The mounting point preferably takes the form of a clip that allows the neck component to be separated from the mask. Secondly, an elastomeric tube is preferably utilised from the mounting point to the mask. The elastomeric tube does not then have to be adjusted in length, but it is able to provide some elasticity in the connection between the neck component and the mask, to thus compensate for changes in the flow generator-to-face distance, as the user moves his or her head. Thirdly a rigid link connection is provided between the mounting point and the neck component. Also, a ratchet mechanism may be mounted on the neck component and working between it and the rigid link to the mounting point. The mechanism is preferably constructed so that it readily allows the rigid link to be shortened, but will not permit it to be lengthened unless a release button is pressed.

In operation this mechanism may typically work as follows. The breathing apparatus may be initially supplied to the user set to the largest size (i.e. with the rigid link set at its greatest length). When the user tries on the breathing apparatus for the first time, they have only to place one hand on the neck component (behind their head) and the other on the front of the mask (in front of their face) and push the two gently together. With this single action it is possible to achieve exactly the desired degree of tension between neck component and mask.

Air Humidity/Temperature Control

In cold and/or dry climates lack of adequate humidity in the air can cause significant discomfort, including drying and cracking of the nasal passages and lips and a feeling of deep cold in the nose. None of the existing PAPR designs offers control of either the temperatures or the humidity of the mask air. The present invention seeks to remedy these deficiencies, rendering the breathing apparatus comfortable to wear/use in any climatic conditions.

FIGS. 9 to 15 illustrate examples of air temperature/humidity control devices which may be typically used in the breathing apparatus of the present invention.

Figure 15:
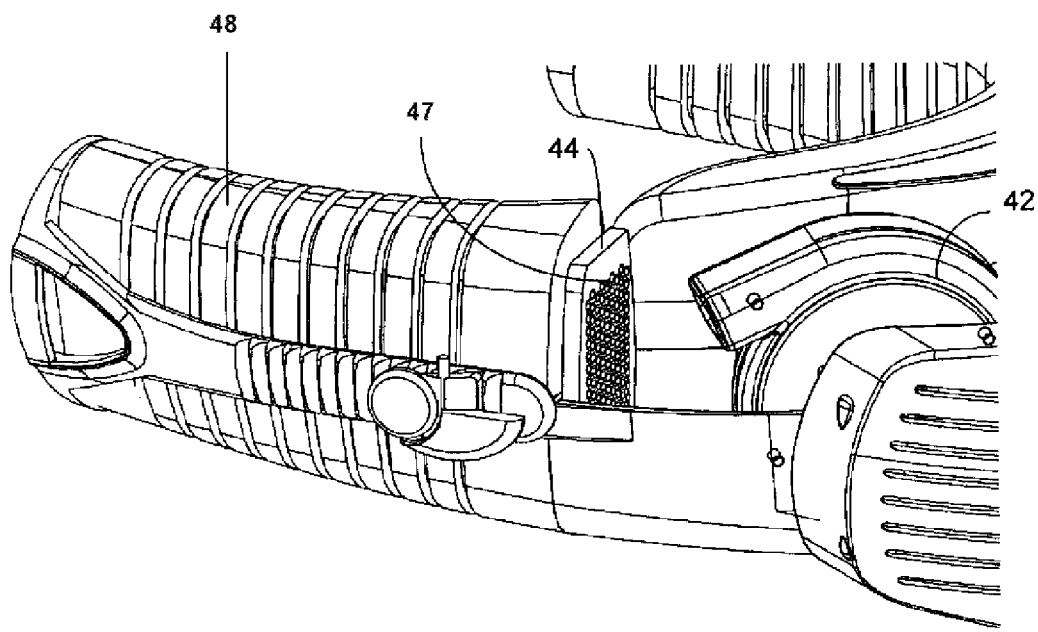
FIG. 15 shows the provision of an alternative heater in the breathing apparatus.

The heater/cooler may be placed anywhere in the air stream, for instance as shown in FIGS. 9 to 12, the heater/cooler 40 directly behind the inlet filter 41, between the filter and the blower or, as shown in FIG. 15, the heater may be placed in the duct between the blower 42 and the duct 48 to the mask, or, in the mask itself.

By way of example, the following types of heating elements may typically be incorporated in the breathing apparatus. These include flexible heating elements (made from copper or nickel-based tracks sandwiched between layers of plastic insulator such as polyester or polyimide) and heated by passing an electric current though them, other heaters consisting of electrically resistive elements, devices using the Peltier effect (which can heat or cool—for instance the Opto-Cooler HV14 device from Nextreme Thermal Solutions), electrically resistive wires within the air path or mask or embedded in the walls of those structures, and/or, heaters in which an electrically conductive ink is printed on a substrate and an electric current passed through it.

Also, by way of example suitable cooling devices may typically include devices using the Peltier effect (for instance the OptoCooler HV14 device from Nextreme Thermal Solutions), and/or, evaporators, in which a liquid is put in thermal contact with the air stream and allowed to evaporate, wherein the energy required to change the fluid from a liquid to a gas is supplied by the air stream, which is cooled as it passes over the liquid.

In a preferred form the device regulates mask air temperature based on readings from a temperature sensor at or near the mask.

Alternatively the device may sense ambient air temperature and then calculate the temperature of the mask air based on its reading (or an estimate) of the air flow rate. In this implementation the device reads the ambient air temperature and (optionally) the air flow rate. It then consults a look-up table of experimentally determined values that tell it how much the air will heat or cool as it passes through the device to the patient. Alternatively the experimentally determined heating/cooling values may be embodied in a mathematical formula that allows the expected mask air temperature to be calculated.

The target mask air temperature is preferably under the control of the user (i.e. the user can set the target temperature). Alternatively the target air temperature can default to some value that most users find comfortable. Ideally the default value may be different depending on the ambient temperature. For instance most users will find a temperature of 30-32 degrees C. comfortable when the weather is cold, but may prefer a lower temperature (perhaps 18-20 deg C.) when the weather is hot.

To control mask air humidity the breathing apparatus may be provided with a water reservoir 43 and a means of producing controlled evaporation. The water tank may be placed inside the flow generator or can be made to clip onto it, or can be located elsewhere (for instance on the user's belt) and provided with a tube or other arrangement for transferring water from it to the evaporator module. It may be convenient to combine the evaporator module with the heating/cooling module.

The evaporator may be placed anywhere in the airstream, for instance directly after in the inlet filter, between the blower and the mask or inside the mask. The evaporator may take many forms, as explained below.

Figure 11:
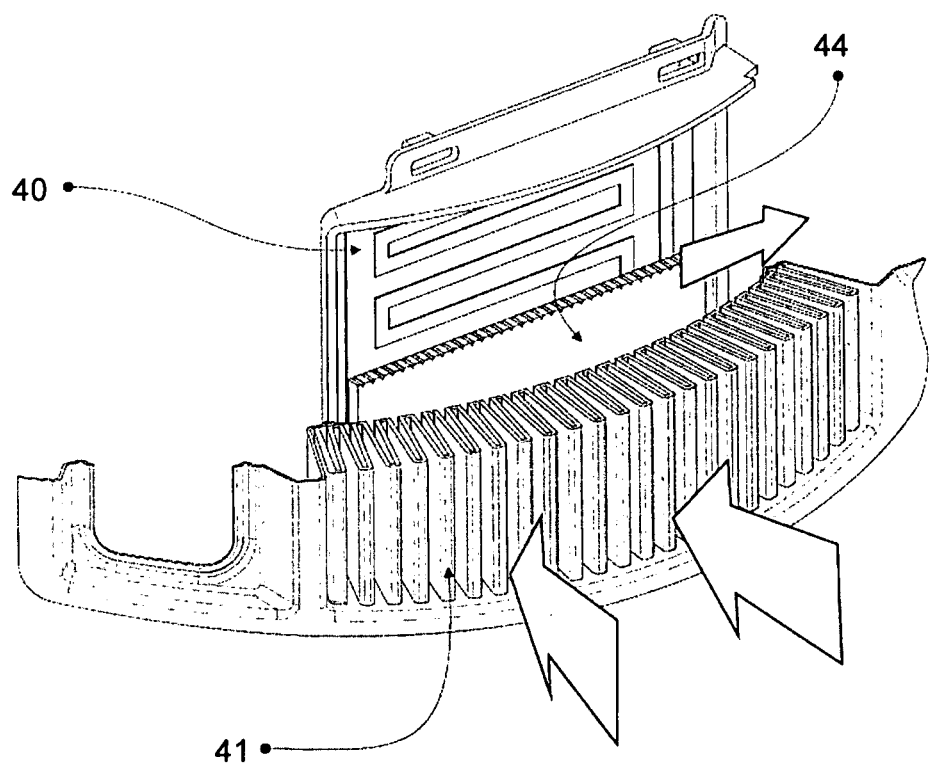
FIG. 11 details an alternative humidifier which may be installed in the breathing apparatus.

One form of evaporator module may be implemented as shown in FIG. 11, having a sheet or roll of a wicking material 44 that automatically transfers water from wet to dry areas. Examples include cloth or other structures made from cotton or burlap or from man-made fibres such as bare fibre-glass. This form of evaporator will preferably be held in close contact with a heater 40 to promote rapid evaporation and also to replace the energy lost when the water changes from liquid to vapour. In this way the cooling effect of evaporation may be regulated or eliminated.

Figure 12:
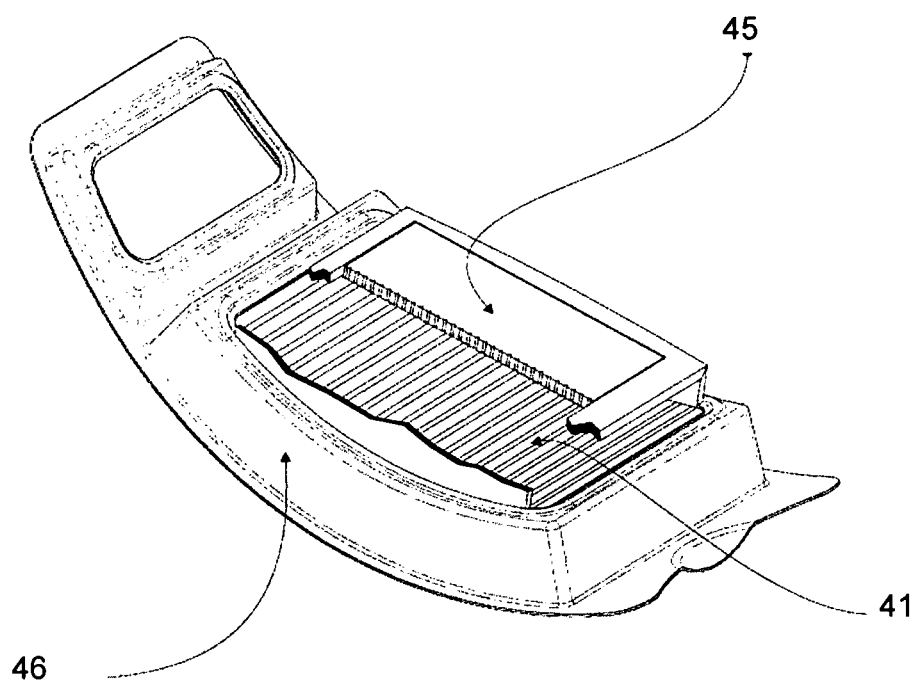
FIG. 12 shows an integrally formed filter and humidifier wick.

Preferably this sort of wick 44 is easily replaced. Regular replacement of the wick is important to avoid the build-up of contaminants from the water (e.g. calcium carbonate) and the growth of organisms on the wick. An example of a wick that is easy to change is shown in FIG. 12. In this example the wicking element 45 has been combined with the filter element 41, which itself is attached to a filter frame 46 so that it is changed every time the filter is replaced.

Figure 13A:
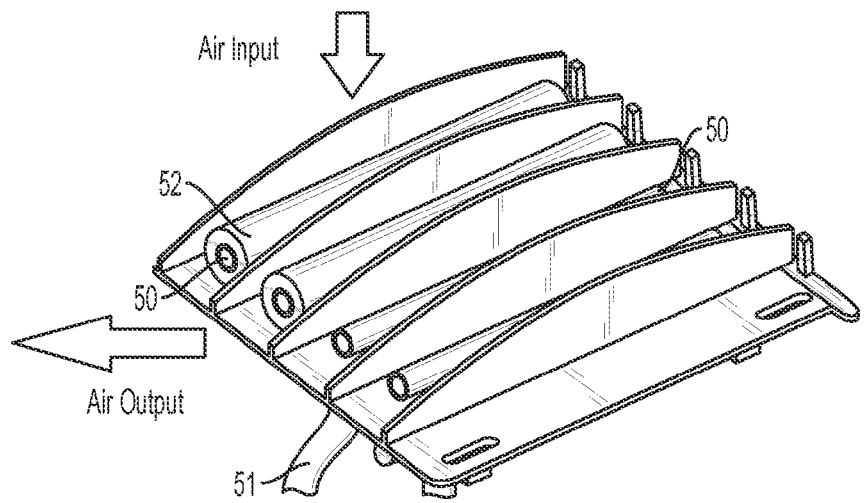
FIG. 13 shows another alternative wicking design for the breathing apparatus.
Figure 13B:
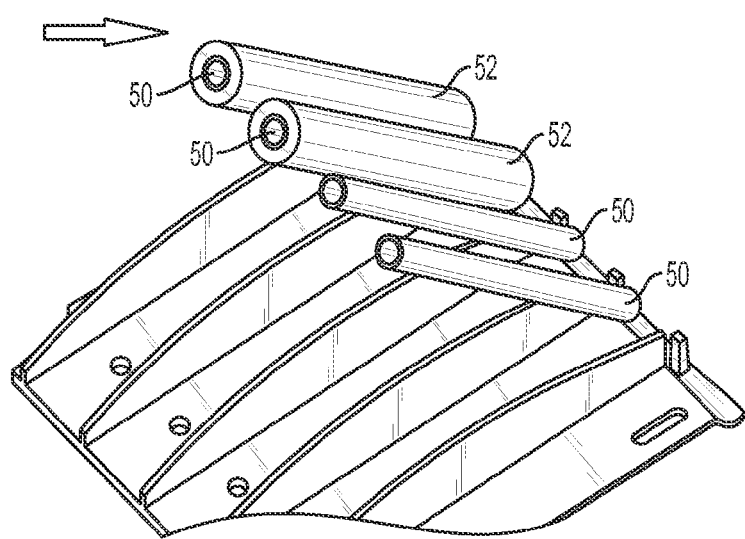
Figure 13C:
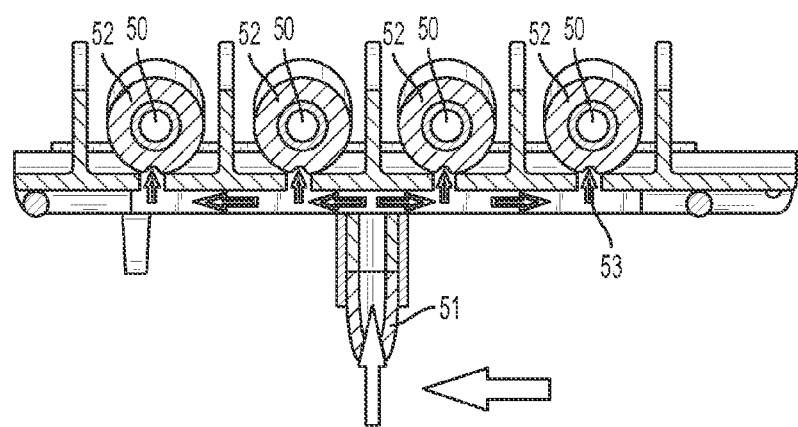

An alternative wicking design is shown in FIG. 13. The heater takes the form of four "fingers" 50, positioned in the air path (shown by arrows) just after the inlet filter. Sleeves of wicking material 52 are fitted over these fingers. Water is supplied to the sleeves 50 from a tank via inlet 51. Heat from the fingers 50 causes the water to evaporate and pass into the air stream.

When the cotton sleeves 52 need to be changed, the structure pivots out into the filter area as shown in FIG. 13B.

Two alternative versions of this design are shown in FIGS. 13 and 14. In the first, as shown in FIG. 13, water is supplied from small nozzles 53 positioned so as to press against the outside of the wicking sleeves 52. In this implementation the heaters 50 may be metal tubes into which resistive wires are placed.

In the second implementation, as shown in FIG. 14, the heating fingers 50 are hollow and are provided with small weep holes 54 around their periphery. Water is introduced into the fingers 50 and makes its way via the weep holes 54 into the wicking sleeves 52 and from there into the air path.

Figure 10:
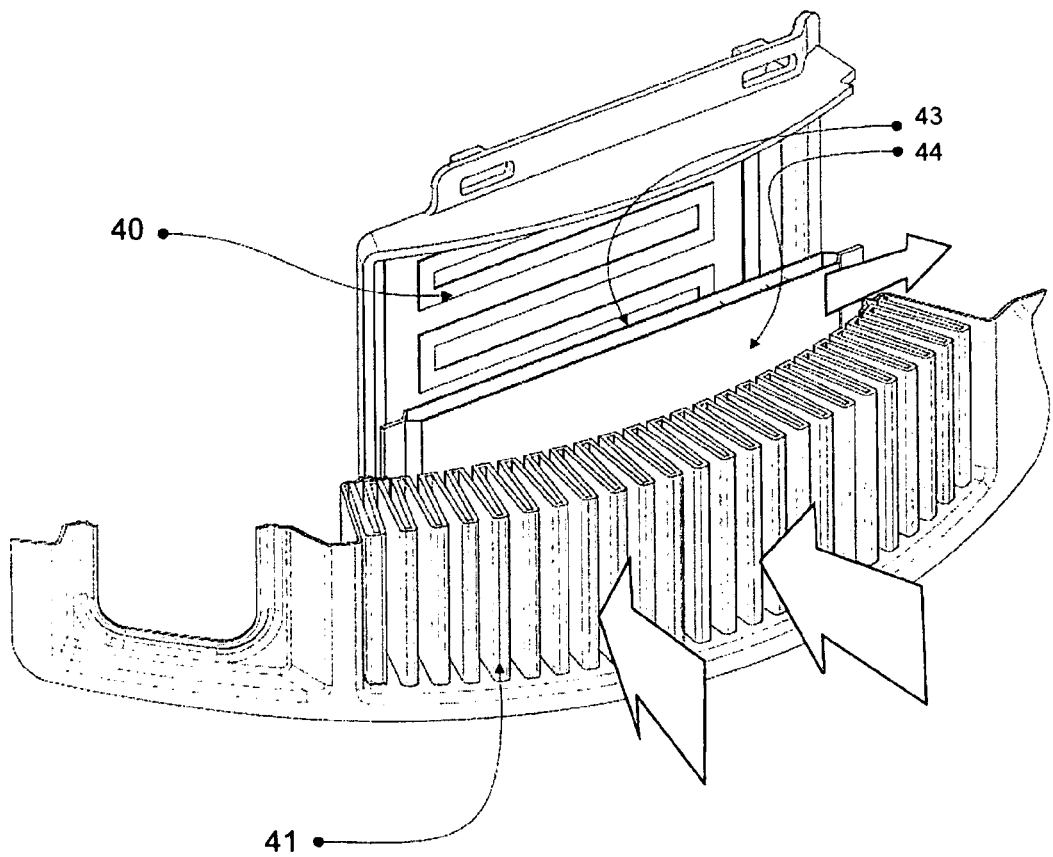
FIG. 10 illustrates the provision of a humidifier which may be installed in the breathing apparatus.

In FIG. 10, an of evaporator module is shown which uses membranes, to separate the liquid water from the air path. These systems consist of a water reservoir 43 covered by a material 44 that allows water vapour but not liquid water to pass.

Examples of this sort of material are expanded PTFE membranes (Gortex by WL Gore and similar) and flashspun high density polyethylene (Tyvek by Dupont and the like). The reservoir may be heated or unheated, although an unheated reservoir will provide low humidity output. In the heated version the water is heated to some high temperature (up to 100 deg C.). Vapour passes through the membrane into the air stream. However the liquid water cannot pass through the membrane, even when the reservoir is agitated or inverted. The reservoir can be a small volume supplied by the main water tank; or it can be the tank itself.

The membrane 44 covering the reservoir 43 is prone to clogging due to contaminants in the water. It is preferable that this membrane be easily changed.

As the joint between the membrane and the rest of the reservoir is subject to some pressure differential (due to the heating of the water and its resistance to vapour flow), the membrane is preferably factory-sealed to the reservoir. In the implementation shown, a reservoir is provided on the back of the filter element. The reservoir has one side made from a vapour-permeable membrane as described above, while the other is made from metal foil. Alternatively, the metal foil may be replaced with a plastic, either in its natural state or coated with a metal (for instance aluminium) to improve its heat transfer characteristics.

When the filter is fitted, the metal-foil side of the reservoir is pressed against a heater mounted within the flow generator. The metal-foil half of the reservoir is sealed (glued or welded) to the vapour-permeable membrane, which faces into the air path. Water is fed into the reservoir from an external tank. Heating the water in the reservoir causes evaporation. The water vapour passes into the air stream, while the liquid remains in the reservoir. Preferably the external tank is sited above the reservoir. If this is done the reservoir will be filled automatically by gravity-feed.

Alternatively the membrane may be provided with some easy method of ensuring a tight seal between itself and the reservoir. Examples include self-adhesive seals and rubber seals. In a design using a self-adhesive seal the replacement membrane is provided with a piece of double-sided adhesive material (for instance VHB tape by 3M). One side of the tape is bonded to the membrane in the factory, while the other side is left covered by a protective covering. To replace the membrane, the old one is removed, the protective covering is peeled from the tape seal and the new membrane is stuck in place. In a design using a rubber seal, a compliant material (for instance a thermo-plastic elastomer such as Santoprene by Exxon Mobil Chemical) is moulded around the edge of the membrane. In use this material is compressed between flange on the reservoir and another component of the flow generator so as to create a seal.

An additional advantage of using a membrane between the water and the air path is that most such membranes can block the movement of bacteria, thus providing a level of protection against the use of contaminated water in the humidifier.

Ideally mask air relative humidity (RH) is controlled by reference to a RH sensor in or near the mask. This sensor will ideally sense both absolute humidity (grams of water per liter of air) and temperature, allowing it to calculate the relative humidity.

Alternatively, the device can sense ambient humidity and then use its knowledge (or estimate) of mask air temperature to infer the relative humidity in the mask.

The target mask humidity may be under the control of the user, for instance by having a "Mask RH" setting in the user interface. Alternatively, the device can target a default value that has been found experimentally to suit most users. This value is generally in the range of 60% to 80% RH.

Alternatively the user can control humidity via an open-loop system in which the user controls the power to the evaporator module.

In some situations, for example, due to manufacturing costs or environmental conditions, a full heating/cooling module with a humidifier is not essential. In a broad range of areas in the northern hemisphere, cold and wet condition may present for quite a long time of a year, such as the United Kingdom, Russia, and Canada.

Instead, a compact heating module 47, as shown in FIG. 15 requiring tittle space in the device and manufacturing cost can be favoured in raising mask air temperature. In the meantime, an easy-fit-removal heating module can be adjusted to a particular market by quickly changing assembly process rather than much effort to modify the device. This heating module embodiment includes three major components, a heating element, heat insulation, and support.

A heating element may be used to generate heat to add to passing air. Various types of heaters suitable in this embodiment, including a PTC heater, highly compact coil heater. The power can be supplied from the PCB with an extra plugging wire just like the other energy consuming parts of the device. An embodiment of a heating module is illustrated in FIG. 15, wherein it is shown that the heating module is provided in the air stream of the breathing apparatus.

PTC is known for its high compatibility and outstanding output performance. This ceramic block can be manufactured to meet different standards with various voltage inputs and output powers.

A thin plate of PTC heater can sit in the air pathway and it is usually made into honeycomb to supply relatively large surface area and structure stability. Air is pumped towards the heated plate and is forced to squeeze through the honeycomb. During this process, heat is picked up by relatively cooler air. Once air leaves the plate and enters the bellow, it has been warmed up.

Coils have a long history as heating elements. Their simple structure enables low tech manufacturing and it can be made highly compact with several rounds of coils in a limited space. In the meantime, its performance has a linear relationship to its structure, and this makes it easy to control.

Similar to the heater in a hair dryer, coils can be added into the air pathway in a module. The large surface area and the least interference to the airflow offer smooth heat transfer. It has been shown that coil heaters are capable of heating a large volume of airflow to a desired temperature.

Flexible heaters consist of high performance heating wires embraced in two layers of dielectric isolation material. With thin aluminium fins attached to the both sides of its surfaces, it has a great potential to distribute heat into air uniformly. Due to its flexibility, this type of heater can be bent into an irregular shape to fit into the air path.

Filter Assembly

Existing PAPRs often need to use specific gas filters for specific gases and often target the environment with rather high gas concentration that demands significant physical size for a given filter. This is not practical for typical city street pollutant protection, where the gas pollutants can be one or all of CO, NOx, SO2, O3, VOCs, smokes, Ammonia, etc but with relatively lower concentration than in a typical industrial environment that most PAPRs target at. This invention describes a special filter in a low profile configuration that in addition to particulate filtration is also capable of filtering most common street gas pollutants from unhealthy to good inside the mask. The gas filtering is achieved by one of or both of an activated carbon filter and photo catalyst filter. Said photo catalyst filter is preferably made in TiO2, and is reactive in all sorts of light, preferably in standard LEDs. This makes UV light unnecessary which helps improve product safety.

Figure 16:
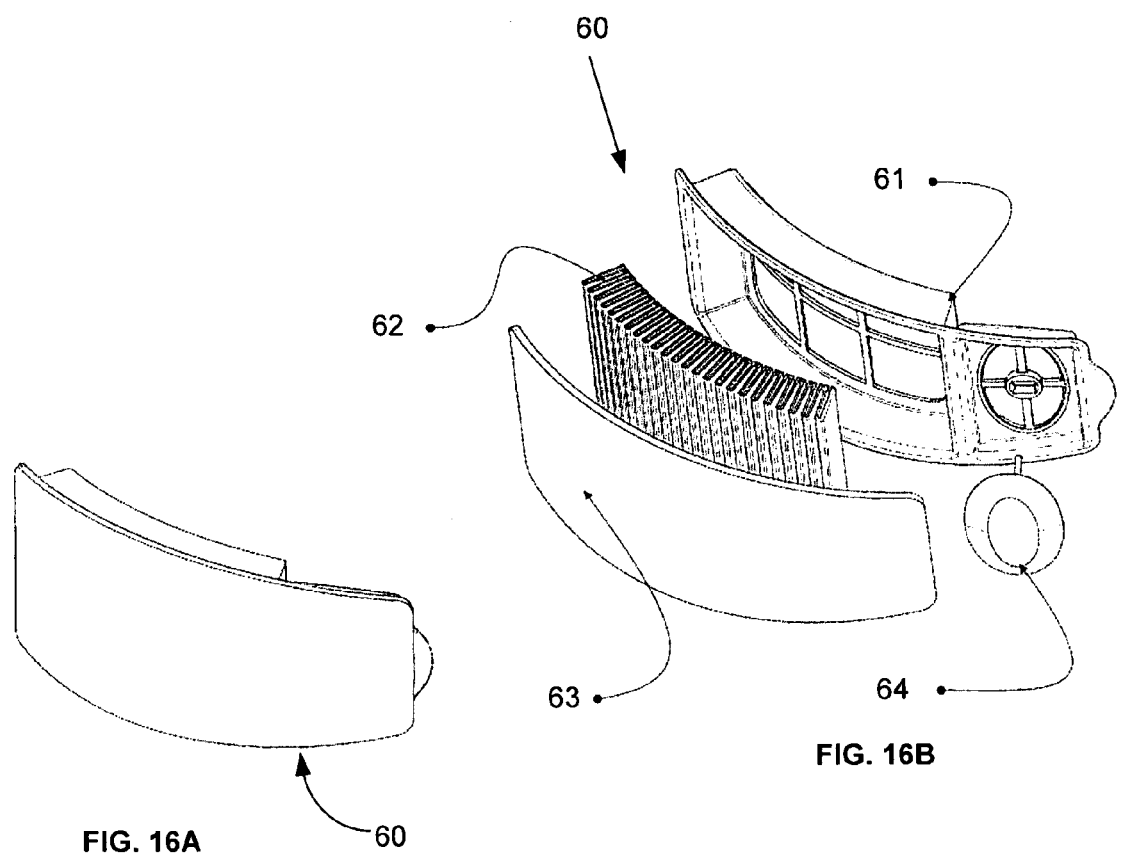
FIG. 16 shows a filter assembly for the breathing apparatus.

The filter assembly, is shown in FIG. 16A in its assembled form, and, in 16 B in exploded form. The filter assembly 60 includes a filter frame 61, a main filter core 62 (illustrated as a HEPA filter), and a particulate filter cover 63. Also shown is a boston valve 64. The filter is preferably housed in a low profile enclosure with a user removable filter cover. The filter cover 63 has multiple openings/slots to let in the air and also to bring in ambient light. The filter cover 63 as well as the enclosure body can be also light transparent. A light reflecting coating can be applied on the inside of said filter cover. Said filter cover is separated with the filter element 62 by a thin gap. The gap provides a space for an even airflow distribution through the filter 62. It also provides space needed for ambient light to be better distributed on the surface of the filter if applicable.

Most existing respirators use valves to control the exhaust air from the mask. The valve closes at inhalation and opens at exhalation. However, this mechanism allows breathed air unfiltered before exiting to the environment. In certain situations, this is undesirable or even harmful to others, such as when a virus infected patient wears the device, or the device is worn by food processing workers. This invention introduces a valve and filter combination for exhaust air. As shown in FIG. 16B, filter 63 provides filtration to exhaust air in combination with valve 64.

Figure 17:
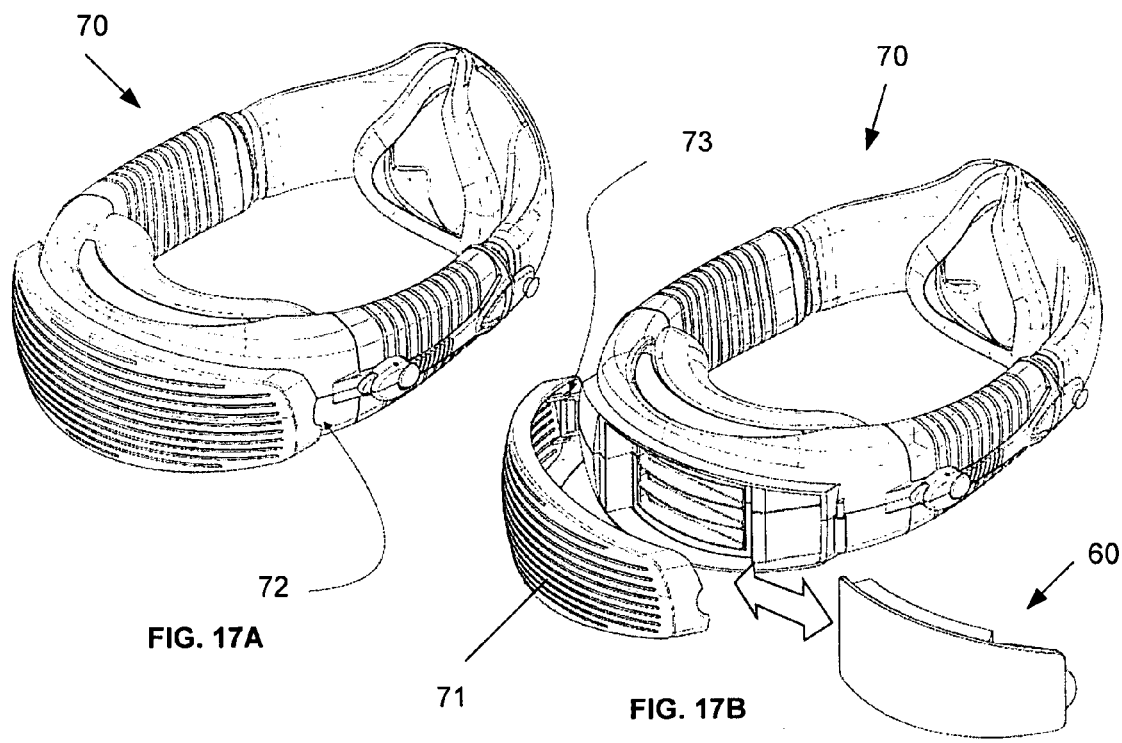
FIG. 17 shows a typical filter replacement procedure.

FIG. 17 shows how the filter may be easily replaced by a user, FIG. 17A showing the assembled unit 70, whilst FIG. 17B showing the unit 70 in exploded form, wherein the filter cover 71 is removed for replacement of the filter 60. To remove the filter, firstly, the filter cover is opened by inserting the user's finger at cutout 72. The filter cover is then able to be moved apart from the unit 70, due to the provision of an over-centre latch 73, such that the filter can then be removed as indicated by the arrow in FIG. 17B.

Various optional types of filters may be alternatively used, as shown in FIG. 18A to 18H.

Figure 18A:
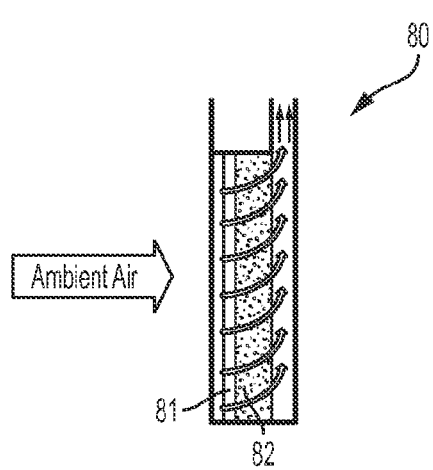
FIG. 18 shows various exemplary configurations of different filter configurations.

In one embodiment, shown in FIG. 18A said filter assembly 80 consists of a pre-filter 81 and a HEPA particulate filter 82. Said pre-filter 81 is the first filter element behind the filter cover 83 and protects said HEPA filter 82. Both said pre-filter 81 and HEPA filters 82 are preferably easily removable by users.

The pre-filter 81 may made from a suitable synthetic fiber such as polypropylene, and preferably with efficiency equal to or better than 90% for particle size of 5 um and above. Said pre-filter 81 is not pleated making it suitable as a base material to be impregnated with photo catalyst media.

Figure 18B:
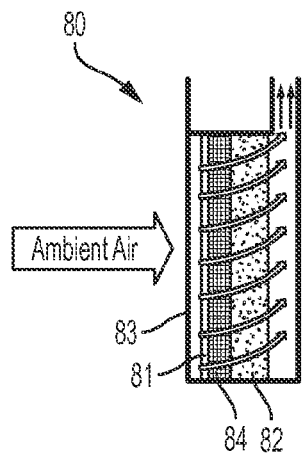

In another embodiment, shown in FIG. 18B, said filter assembly 80 consists of a pre-filter 81, an activated carbon filter 84 and a HEPA particulate filter 82. Said pre-filter 81 is the first filter element behind the filter cover 83 and protects said activated carbon 84 and HEPA filter 82. All filters are easily removable by users.

Figure 18C:
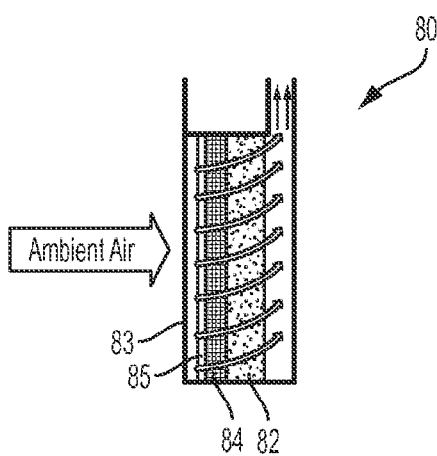

In another embodiment, shown in FIG. 18C, said filter assembly 80 consists of a photo catalyst media plus pre-filter 85, an activated (typically steam activated) carbon filter 84 and a HEPA particulate filter 82. Said pre-filter 85 is the first filter element behind the filter cover 83 and protects said activated carbon 84 and HEPA filter 82. All filters are easily removable by users. Said photo catalyst media 85 is activated when daylight is available. Once activated, said photo catalyst media 85 will work to breakdown typical harmful gas pollutants.

Figure 18D:
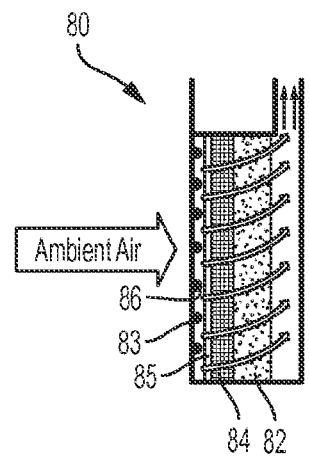

In another embodiment, shown in FIG. 18D, said filter assembly 80 consists of a photo catalyst media plus pre-filter 85, an activated carbon filter 84 and a HEPA particulate filter 82. Said pre-filter 85 is the first filter element behind the filter cover 83 and protects said activated carbon 84 and HEPA filter 82. All filters are easily removable by users. An array of LEDs 86 is mounted on the backside of said filter cover 83. Said LEDs 86 can also be mounted around the wall of the enclosure close to the inlet. Said LEDs 86 and circuit is encapsulated in a bio-compatible film or cover. Preferably, said LEDs 86 are turned on only when ambient light intensity falls below a pre-defined threshold, which is monitored by a light sensor. Hence, said photo catalyst media can always be activated if needed even when ambient light is not available or insufficient.

Figures 18E, 18F:
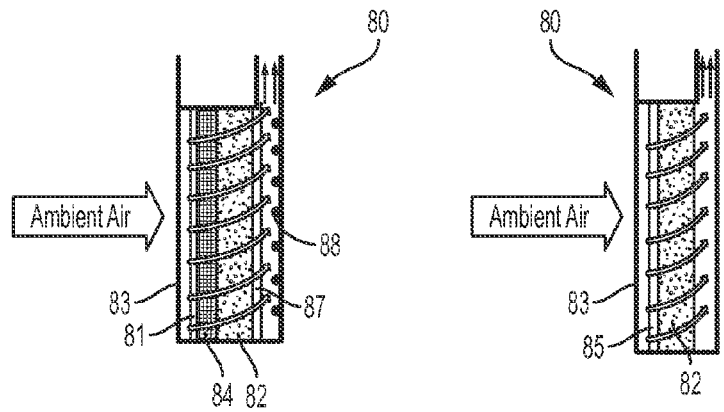

In another embodiment, shown in FIG. 18E said filter assembly 80 consists of a pre-filter 81, an activated carbon filter 84, a HEPA particulate filter 82, and an outlet side photo catalyst media filter 87. Said pre-filter 81 is the first filter element behind the filter cover 83 and protects said activated carbon 84 and HEPA filter 82. All filters are easily removable by users. An array of LEDs 88 is mounted on the inside of the enclosure wall facing the outlet of said photo catalyst filter 87. Said LEDs 88 can also be mounted surround the wall of the enclosure close to the outlet. Preferably, said LEDs 88 are turned on only when ambient light intensity falls below a pre-defined threshold, which is monitored by a light sensor. Hence, said photo catalyst media 87 is always activated even when ambient light is not available or sufficient. Said LEDs 88 and circuit is encapsulated in a bio-compatible film or cover.

In another embodiment, shown in FIG. 18F said filter assembly 80 consists of a photo catalyst media plus pre-filter 85 and a HEPA particulate filter 82. Said pre-filter 85 is the first filter element behind the filter cover 83 and protects said HEPA filter 82. All filters are easily removable by users. Said photo catalyst media 85 is activated when daylight is available. Once activated, said photo catalyst media will work to breakdown typical harmful gas pollutants.

Figures 18G, 18H:
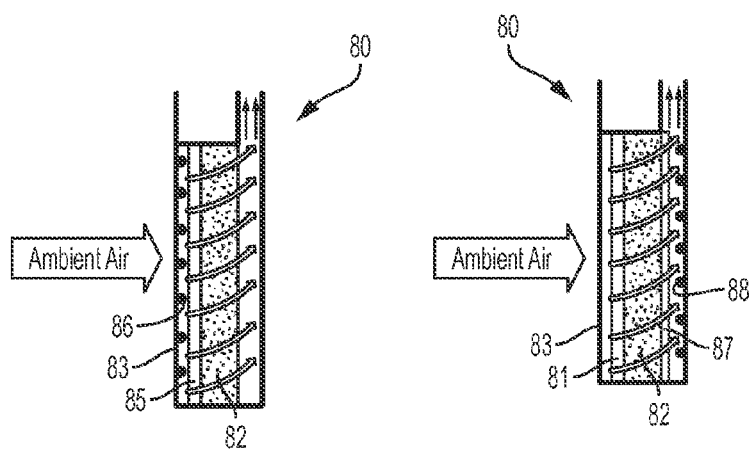

In another embodiment, shown in FIG. 18G said filter assembly 80 consists of a photo catalyst media plus pre-filter 85 and a HEPA particulate filter 82. Said pre-filter 85 is the first filter element behind the filter cover 83 and protects said HEPA filter 82. All filters are easily removable by users. An array of LEDs 86 is mounted on the backside of said filter cover 83. Said LEDs 86 can also be mounted around the wall of the enclosure close to the inlet. Said LEDs 86 and circuit is encapsulated in a bio-compatible film or cover. Preferably, said LEDs 86 are turned on only when ambient light intensity falls below a pre-defined threshold, which is monitored by a light sensor. Hence, said photo catalyst media 85 can always be activated if needed even when ambient light is not available or insufficient.

In another embodiment, shown in FIG. 18H said filter assembly consists of a pre-filter 81, HEPA particulate filter 82 and a photo catalyst filter 87. Said pre-filter 81 is the first filter element behind the filter cover 83 and protects said photo catalyst media filter 88 and HEPA filter 82. All filters are easily removable by users. An array of LEDs 88 is mounted on the inside of the enclosure wall facing the outlet of said photo catalyst filter 87. Said LEDs 88 can also be mounted surround the wall of the enclosure close to the outlet. Preferably, said LEDs are turned on only when ambient light intensity falls below a pre-defined threshold, which is monitored by a light sensor. Hence, said photo catalyst media 87 is always activated even when ambient light is not available or sufficient. Said LEDs 88 and circuit is encapsulated in a bio-compatible film or cover.

Figure 18I:
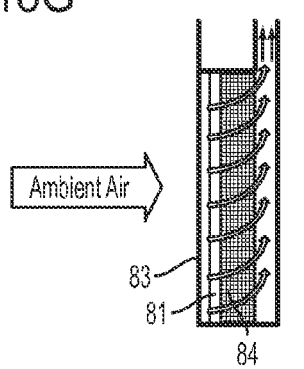
Figure 19A:
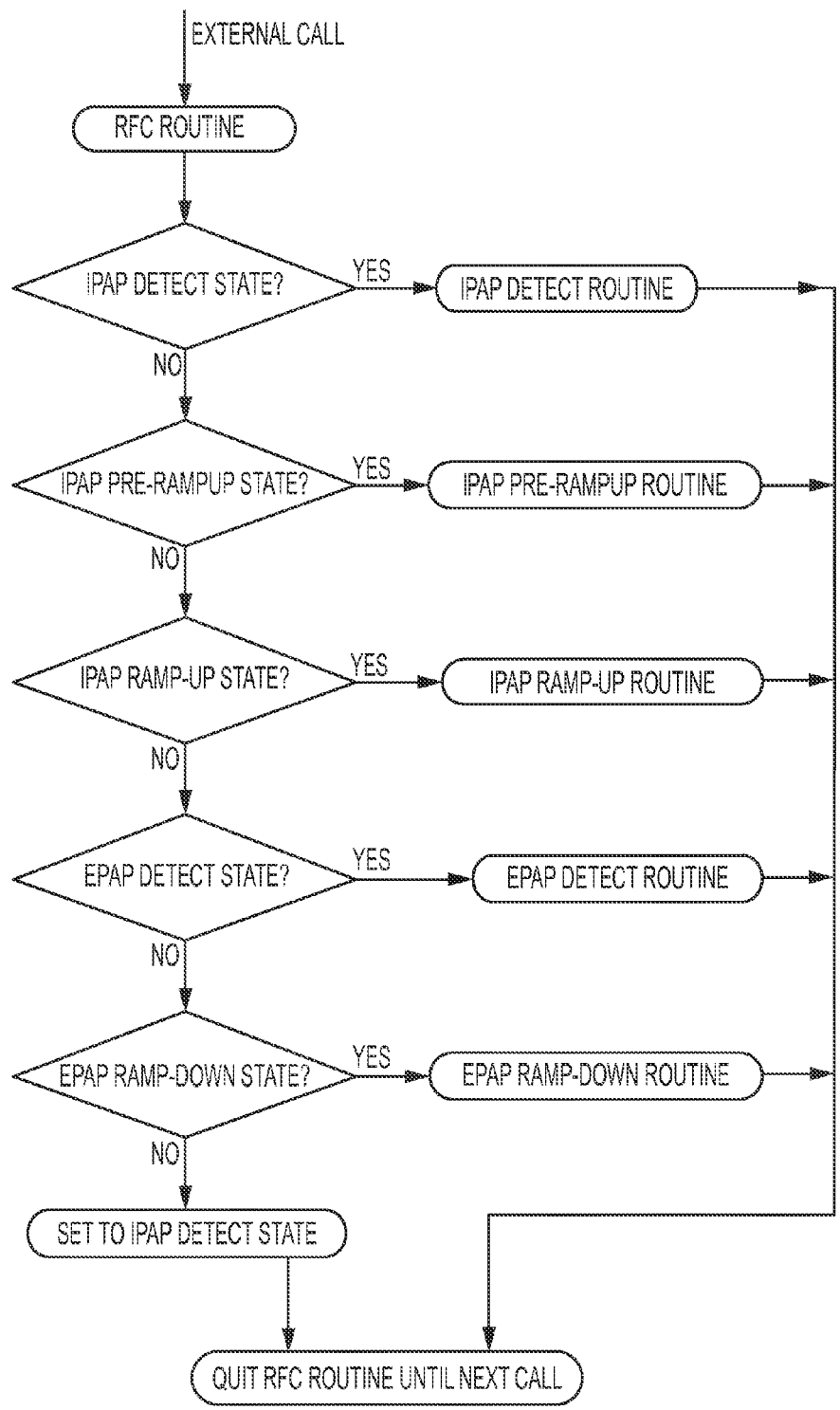
FIG. 19 shows various exemplary flowcharts of the steps used in the responsive flow control of the flow generator module of the present invention.
Figures 1, 19B:
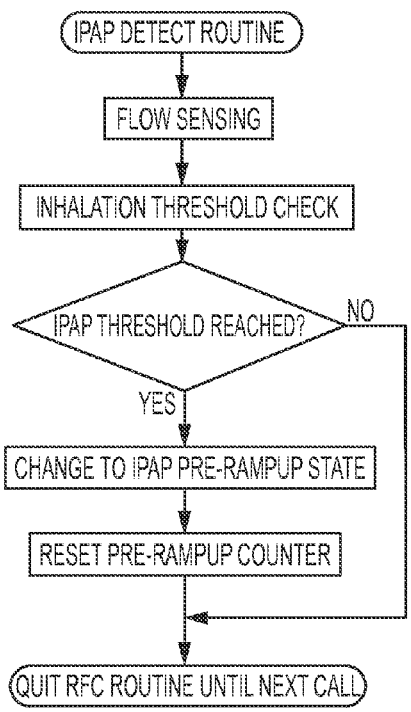
Figures 2, 19B:
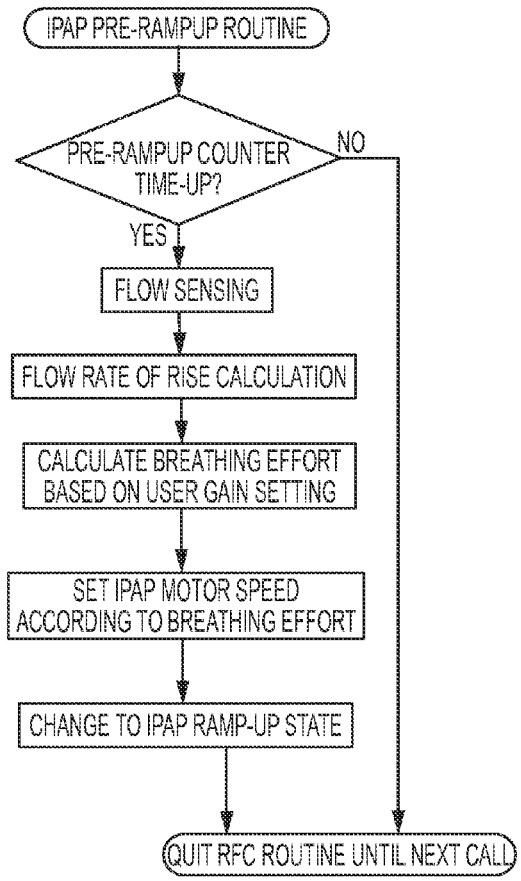
Figure 19E:
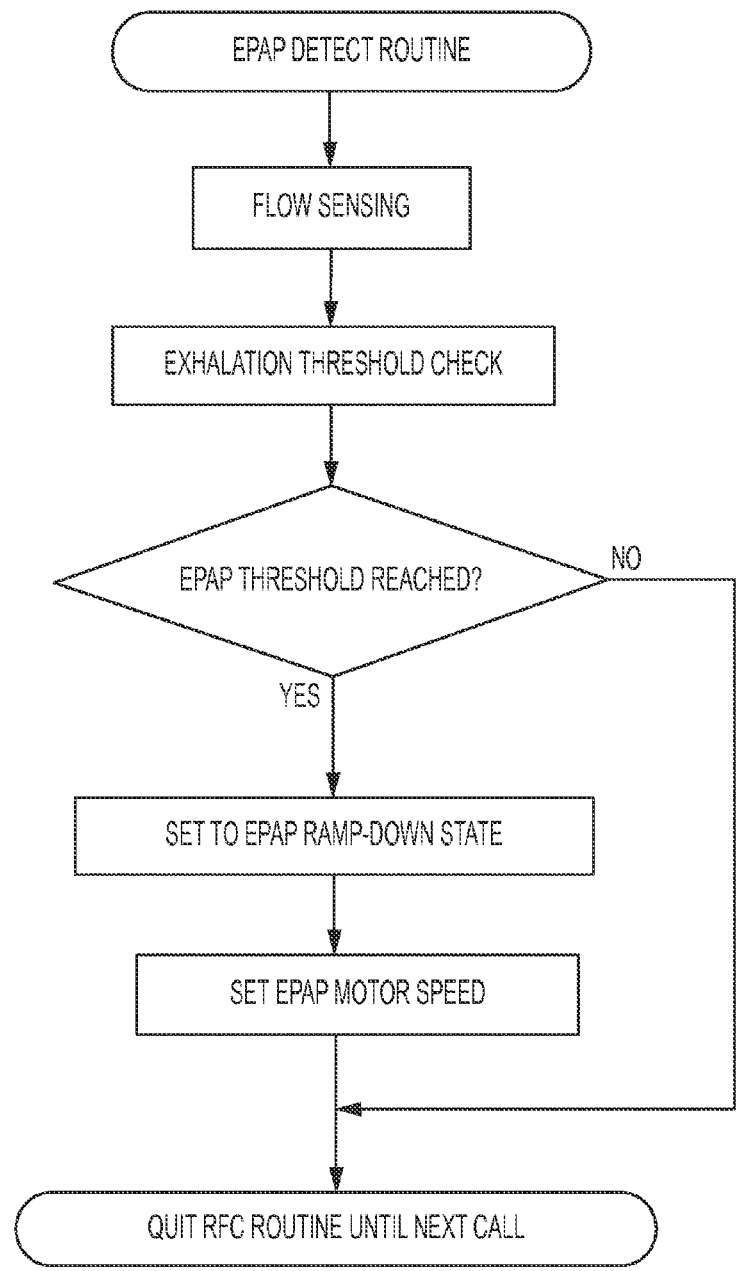

In another embodiment, shown in FIG. 18I, said filter assembly consists of a pre-filter and an activated carbon filter. Said pre-filter is the main particulate filter selected to provide the required particular filtering efficiency in addition to protect said carbon filter. Both said pre-filter and carbon filter are preferably easily removable by a user.

The pre-filter and activated carbon filter can be stacked up as one user replaceable assembly, such as by a simple heat gluing process. The activated carbon, said HEPA and photo catalyst filter can also be stacked up as one assembly.

This HEPA filter preferably has 99.97% efficiency for particulates equal or above 0.3 um, which is equivalent to performance offered by most PAPRs. Said HEPA filter is preferably made of fibreglass paper that is suitable for filtering solid and liquid particles.

The activated carbon and photo catalyst filter work in a complementary fashion—said activated carbon filter provides a general preliminary filtering for most harmful gases by blocking the harmful gases and slow them down, it also works better in removing odours and VOCs, such as formaldehyde; while said photo catalyst filter continue to work specifically to decompose the harmful gases to water and $CO_2$, in particular, CO, $NO_2$, $SO_2$, $O_3$, and ammonia. It can also sterilize air which may contain germs, bacterial and virus.

The LEDs can be turned on/off by a user to control sterilisation of the filter even when the device is not in use, such that germs and virus are not built up. The LEDs can be turned on and off in sync with one's breathing. The LEDs can be any standard LEDs or UV LEDs. A light chamber matching the size and shape of said photo catalyst filter is used to transmit light from said LEDs. Preferably, a thin diffuser film is used to transmit light evenly from said LEDs. Said diffuser film also isolates the LEDs from the air path. The activated and photo catalyst filter combination preferably have minimum 90% efficiency to CO, NO2, SO2 and O3 and work at this efficiency for at least 240 hours.

The photo catalyst media can also be applied as a coating inside said mask and neck components. The coating can be a complementary measure to kill or inactivate most virus and bacteria when exposed to visible light.

For all the filter configurations described above, an optional coarse filter can be added before the pre-filter to remove rather large particles often present in dustier environments, such as wood cutting workshops. Said coarse filter may be in low cost synthetic fibre and washable or easily disposable, thus enabling longer use of the main filter.

Said filters described above may be in any order or in different combinations.

Responsive Flow Control, Etc

FIGS. 19A to 19E show various flow charts of the steps which may be used in the responsive flow control of the flow generator module of the present invention, whereby the amount of air provided to the breathing chamber is breath responsive, and, the responsiveness is preferably also user adjustable.

Figure 20A:
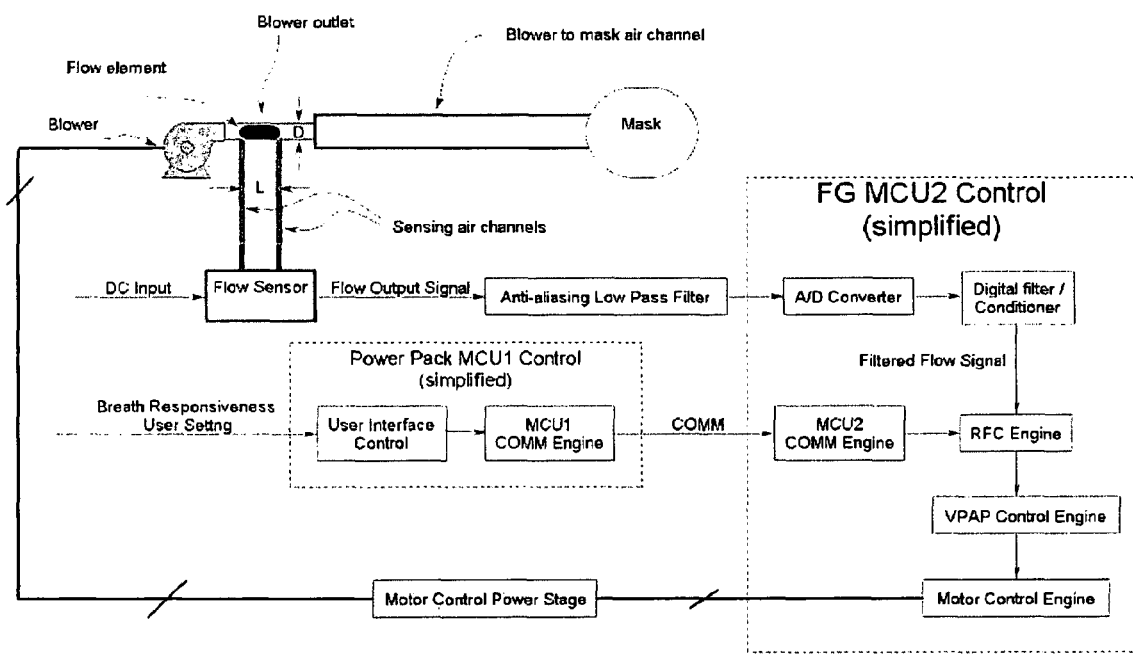
FIG. 20 shows embodiments of a responsive flow system in accordance with the present invention.
Figure 20B:
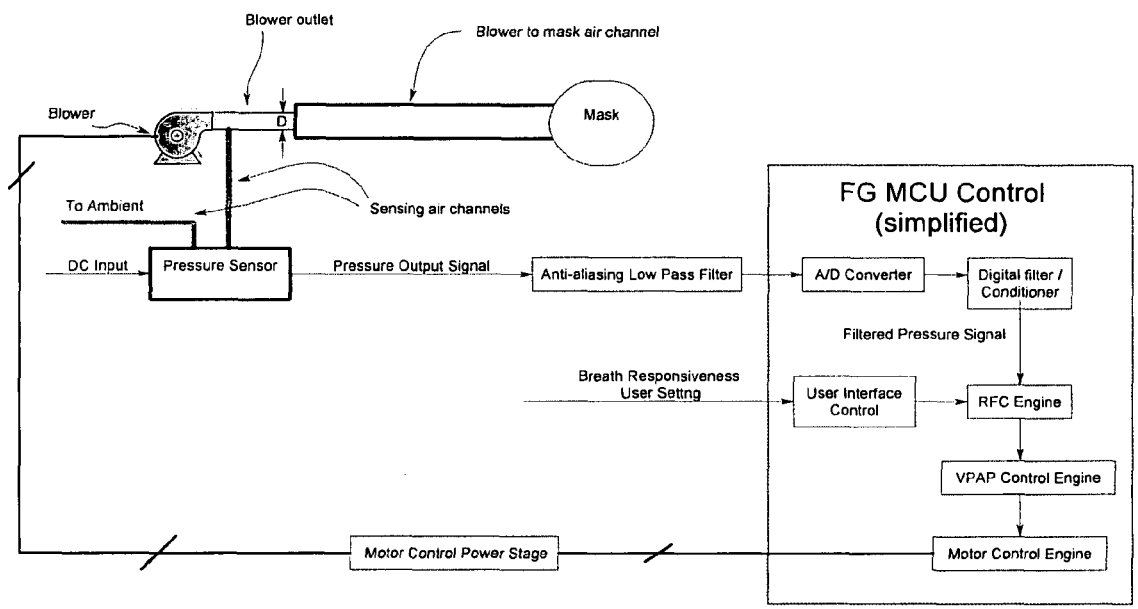

FIGS. 20A-20B show a system diagram of examples of a responsive control system in accordance with the present invention.

Most existing devices do not have flow control on a breath by breath basis except those high end industrial/military types. Even when they do have flow control, they are not responsive enough to breathing effort and the responsiveness is not user adjustable. Rather, a pressure sensor is often used to help maintain a positive pressure at the mask. More air will be delivered to user's mask when the mask pressure goes towards zero, either by increasing the motor speed or by controlling an airflow regulator (USPC Class: 12820423). However, such a control mechanism tends to deliver insufficient flow to the wearer, especially during demanding breathing situations thus causing a sensation of discomfort.

None of the existing devices have the capability to allow direct detection of breathing effort on a breath by breath basis. Some other respiratory apparatus may have user configurable variable positive air pressure control, however, this is a fixed setting and not adaptive to one's real time breathing effort. As a result, the flow control is harsh and not natural which limits the comfort one may receive.

None of the existing devices have the capability to allow user to adjust the responsiveness of the flow control. However, in the real world, different people may have different demands for airflow. Even for the same person, the demand for airflow may vary from time to time. For example, for a respiratory deficient patient, due to the weaker lung function, he or she may not have the same strength to breathe as a normal person. He or she may have the need to get more airflow with a breathing effort that is considered very weak by a normal person's standard. He or she may also wish to have the flexibility to control the airflow by his or her own breathing effort, even it is normally weaker than a normal person, so that he or she can breathe in a more natural way than that a harsh fixed control would allow.

The present invention uses either flow or pressure sensor to monitor user's breathing effort. The rate of rise in airflow at the start of the inhalation is used as a signal to gauge user's breathing effort. The higher the value, the bigger the breathing effort. The MCU then calculates the amount of flow required based on a user adjustable gain control or breath responsiveness setting. The target motor speed is then set at a value corresponding to the breathing effort at the start of the inhalation. Vice versa for the smaller values, where the target motor speed will be set at a lower value accordingly.

This feature will be beneficial to respiratory impaired patient, as their lung muscles can be weaker than a normal person. The user can increase the gain to make the blower more sensitive to flow change, so he or she doesn't have to breathe hard when more air in needed. This will relieve the breathing effort for these patients and let the machine do the hard work. Hence, it improves comfort and provides health benefits to these patients.

The responsive flow control system, shown in FIG. 20 is one of the preferred features of the system of the present invention, and it is a general term that relates to the main function of said flow generator and its communication with said user interface control.

In one embodiment, the function of responsive flow control consists of a blower, a flow sensor with sensing air channels, a flow element, a blower outlet, a blower to mask air channel, an anti-aliasing low pass filter, a motor control power stage, a flow generator MCU2 based control which consists of a A/D converter, Digital filter/conditioner, a RFC Engine, a VPAP Control Engine, a Motor Control Engine, a MCU2 COMM Engine. In addition, it also consists of a User Interface Control and a MCU1 COMM Engine.

The blower produces airflow according to said flow generator control. The motor speed determines the amount of flow to said mask.

The flow sensor detects flow according to pressure drop across said flow element. In a preferred embodiment, said flow sensor is a mass flow sensor, based on thermo-anemometer flow sensing principle, and has analog output proportional to said pressure drop. In a preferred embodiment, said flow sensor has low input pressure range, typically around 0.2" full scale, and said flow element is in fact a section of said blower outlet with L around 5 to 40 mm. The blower outlet is typically in a round shape with a diameter D around 10 to 19 mm but it can also be of any other shape with similar cross-section. The sensing air channels are preferably silicone tubes of suitable diameter.

In a preferred embodiment, said anti-aliasing filter is formed by a simple RC network with cut-off frequency between 100 Hz to 1 kHz. The signal output of said anti-aliasing filter is sampled by said A/D converter at 50 kHz before being further processed by said digital filter/conditioner. Said digital filter has cut-off frequency around 30 Hz with 20 to 80 dB roll-off per decade. The output of said digital filter/Conditioner is fed to said RFC Engine at the frequency of said digital filter cut-off frequency.

The operation of said RFC Engine is illustrated through FIGS. 22A-22B. Said RFC Engine works as a state machine, and its input contains the filtered flow signal and the user setting on the breath responsiveness, and its output contains the target motor speed and breathing state. The RFC Engines runs at frequency of that of the output of said Digital filter/conditioner and starts at IPAP Detection for inhalation detection. Once detected, it samples said tittered flow signal at the first to third entry of said RFC Engine after the IPAP Detection event entry and the differences from said filtered flow signal at the IPAP Detection event entry is recorded. The recoded data is essentially the rate of rise in flow and is used as a gauge fir breathing effort. The final breathing effort is derived after consideration of user breath responsiveness setting or gain control on a breath by breath basis. A look-up table containing motor target speed against breathing effort is then used to output the required motor target speed to said VPAP Control Engine to control the motor speed in a variable positive air pressure fashion. Said RFC Engine continues to monitor breathing state, and to complete the VPAP cycle according to sequences illustrated in FIG. 13 before repeating it for every breath.

The motor control engine contains the motor driver firmware necessary to drive said motor. The motor control power stage contains power switches, their drivers and motor current sensing necessary to facilitate the driving of said motor.

The user interface control receives user setting on breath responsiveness or gain control before transferring it to the flow generator control. In a preferred embodiment, the transfer of user setting is delivered via a single wire communication protocol between MCU1 COMM Engine and MCU2 COMM Engine.

The implementation of the responsive flow control can be achieved with other embodiment with the same spirit of the above embodiment.

In another embodiment, the flow sensor may have other suitable input pressure range. The flow sensor can also be piezo-resistive type, and said flow element can be a laminar flow element. The sensing air channels can be also part of the molding structure for direct coupling to said sensor ports. The flow sensor can also have digital output. Said user setting can also be passed on to said flow generator control by any other suitable means.

In yet another embodiment, a pressure sensor can also be fitted at the similar location of the flow sensor, where the pressure sensor can detect the air pressure at the flow generator outlet. In contrast with the flow sensor embodiment, said pressure sensor detects the rate of reduction in pressure at the start of the inhalation. The MCU then calculates the amount of pressure required based on a user adjustable gain control or breath responsiveness setting. The target pressure is then set at a value corresponding to the breathing effort at the start of the inhalation. The control for the target pressure is preferably done via a proportional, integral and derivative (PID) control but it can also be done by any other suitable schemes.

In a more advanced embodiment, the pressure sensor can be mounted inside the mask, either in wired or wireless fashion.

The benefits of negative ions to humans are well known. However, none of the existing PAPRs employ a negative ion generator. A small negative ion generator is mounted downstream of the blower, with two electrodes being exposed in the air path so that the ions generated can be carried along the airflow to the user's airway.

The negative ion generator can be either a suitable standalone device that can be purchased off the shelf, or it can be customised completely or partially to fit in the application.

The negative ion generator is preferably turned on only when motor runs to save energy and to increase life time. Its control can also be in sync with breathing (on with inhalation and off with exhalation) to further save energy and to increase device life time.

Improved Manufacture and Mounting of a Toroidal Core for a Brushless DC Motor

Due to the particular requirements of the breathing apparatus, a new manufacturing and mounting arrangement has been developed for a toroidal core of a brushless DC motor, which is useful in the breathing apparatus of the present invention.

Examples exist in the prior art of brushless DC motors in which the stator is constructed by winding six coils around the periphery of a toroidal ferrite. This construction yields a compact motor which is very desirable in some applications, for instance in a low-profile PAPR.

Significant problems with toroidal motors have however limited their usefulness to date. These include, firstly, that it is extremely difficult to keep the six coils separate. When the second layer of windings on each coil is formed, it tends to fall off the side of the first layer and migrate into the area reserved for the next coil. This difficulty has lead to the coils generally being wound by hand, which is not practical for volume production. A further problem which occurs is that after the coils have been wound, the resulting stator is of an irregular shape (the coils not being completely uniform) and it has no protruding features to form mounting points. However it is necessary to mount the stator very accurately concentric with the rotor.

A solution which largely eliminates both problems with toroidal motor construction and so opens the way for the wider use of this type of motor, has therefore been developed, and will be described in relation to FIG. 21.

Coils are routinely machine-wound on toroidal cores for other applications, for instance transformers. The difficulty in machine-winding toroidal motor cores stems from the need to place six small coils 91 around the periphery of the toroid 90 and prevent them overlapping, as shown in FIG. 21A.

Many machines are available for winding transformer cores, for instance the RWE series from RUFF Gmbh and the STW-60 from Shining Sun Enterprise Co Ltd. Core winding is significantly cheaper and more accurate with one of these machines than by hand. However these machines can only be used where the outer face of the core is a plain cylinder without protruding ribs. This restriction makes it difficult to design a part or fixture to keep the six coils required for a motor apart. A further difficulty is that any part that is designed to be left in place when the coils are wound must be of a material that is not electrically conductive—generally polymers. In small motors this restriction makes a separate coil-separator component too flexible to be of practical use.

Figure 21A:
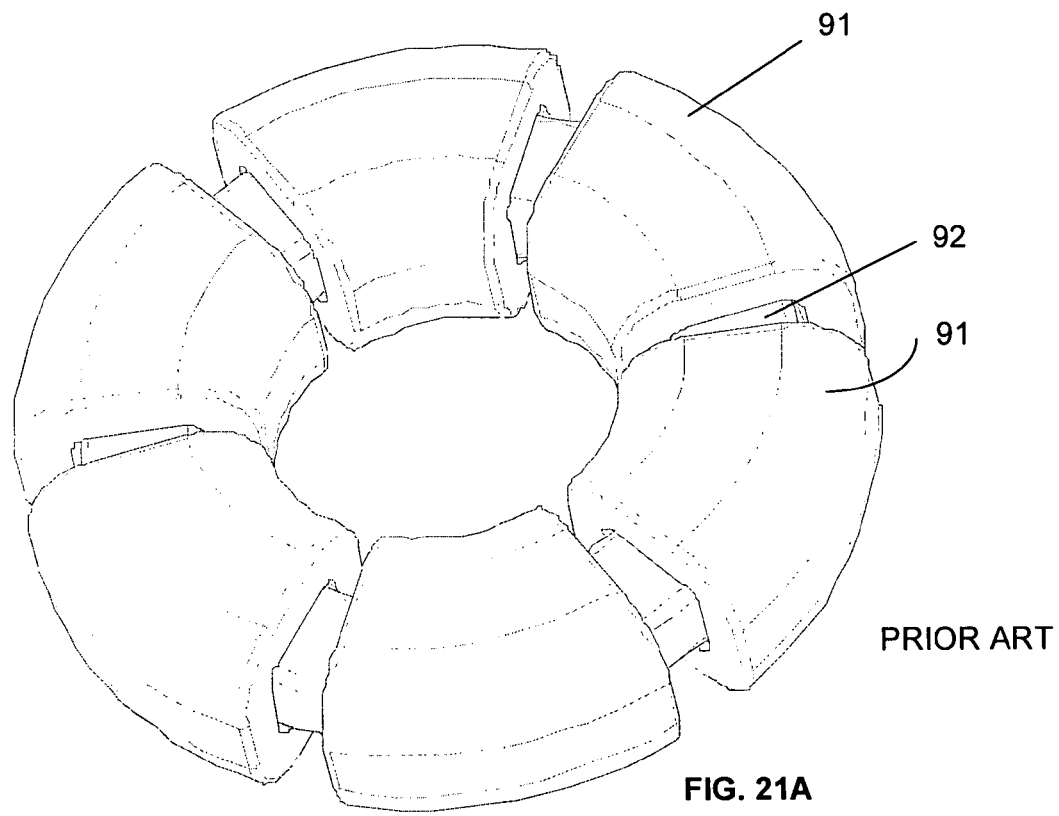
FIG. 21 details a toroidal core arrangement for use in the breathing apparatus of the present invention.
Figure 21B:
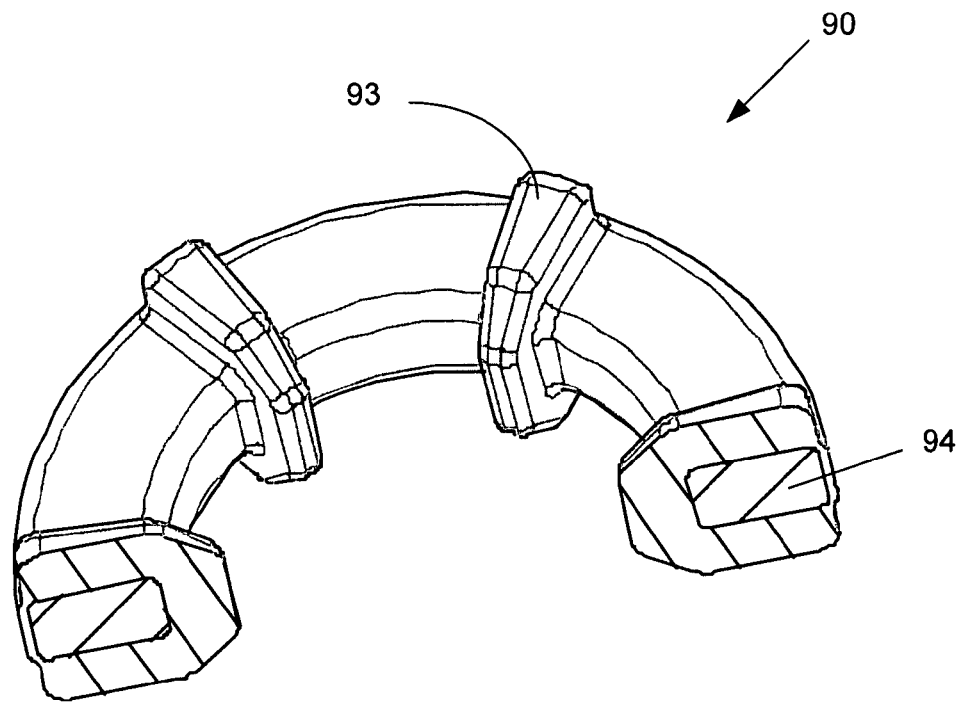

The present invention overcomes these problems by placing radial fins 93 on the core 94, forming a divide between each of the six coils 91 and its neighbor, as shown in FIGS. 21A and 21B. It has been found by experiment that the fins do not need to protrude onto the outer cylindrical surface of the toroid, and for this reason the resulting core is still suitable for winding using standard machines.

Figure 21C:
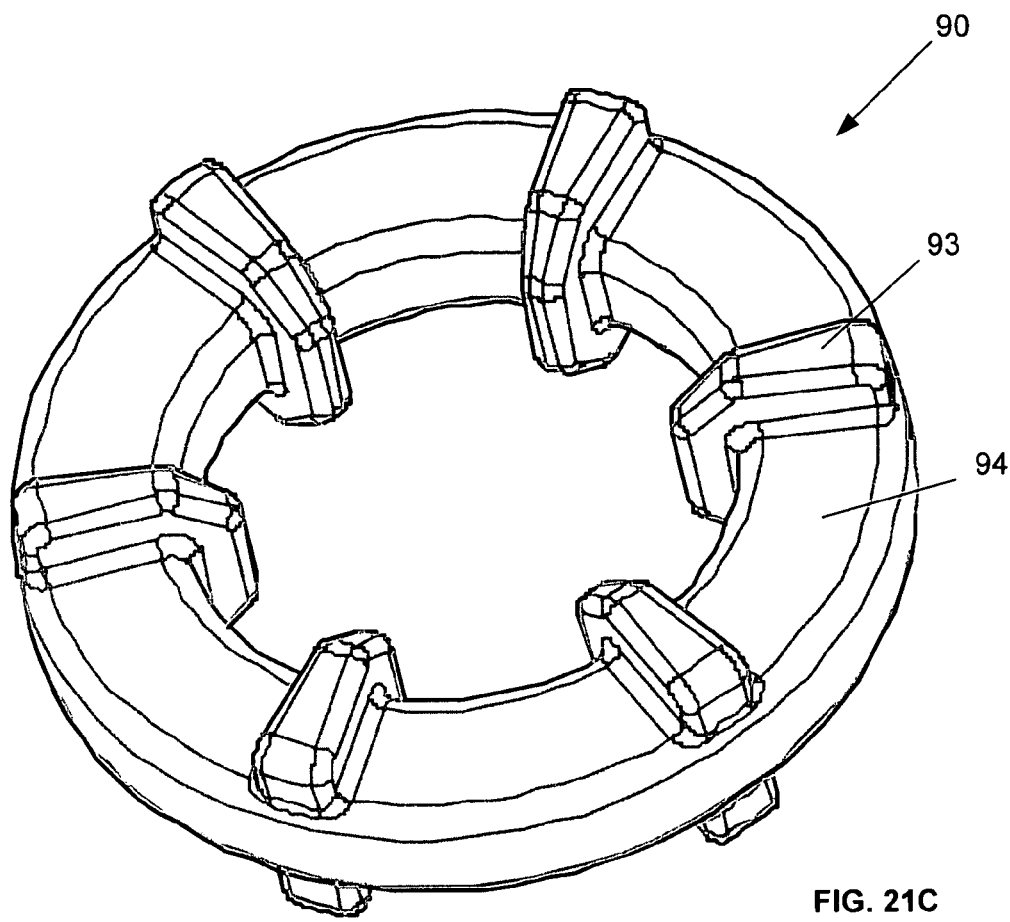
Figure 21D:
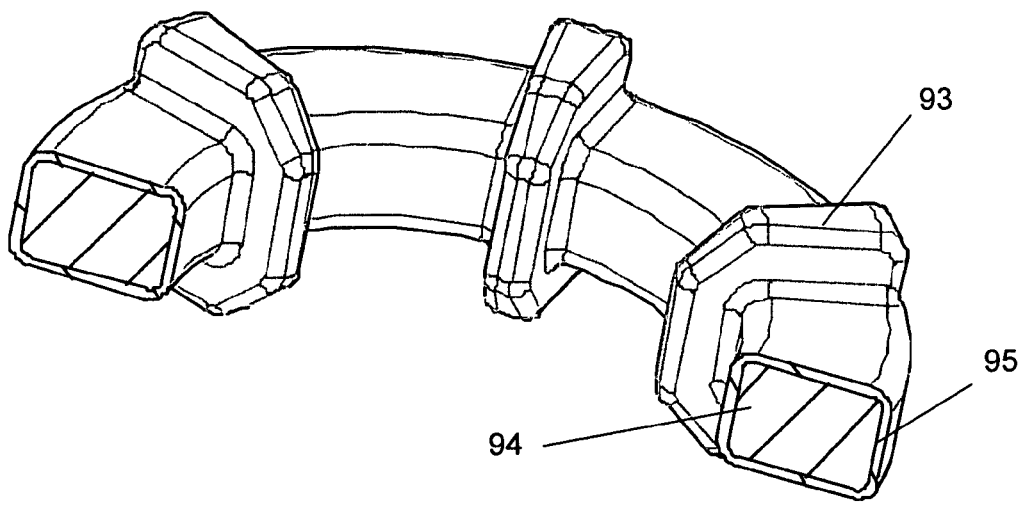

The fins 93 can be formed successfully in two ways. Firstly, they can be formed directly as shown in FIG. 21C, in the toroidal ferrite 94. For this method it is necessary to form the ferrite by injection molding, rather than the usual sintering process. Secondly, they can be formed as shown in FIG. 21D by over-molding a conventional toroidal ferrite core 94 with a stiff polymer 95.

In practice it has been found that the second method is generally more practical. However the ferrite material is brittle and the cores vary significantly in size. For this reason it is necessary to encapsulate most or all of the toroid in plastic, not attempting to blank-off against the toroid except where absolutely necessary to maintain concentricity between core and over-mould. Such a design demands a polymer capable of flowing into very thin sections, but still very stiff (to resist the winding machine). Suitable polymers include polyamides (Nylons), liquid crystal polymer, Polybutylene Terephthalate (PBT) and various others.

The amount by which the fins 93 protrude into the interior of the toroid should be limited as much as possible to ensure that a standard winding machine can be used. However it has been found by experiment that fins the same height as the finished windings can be wound on standard winding machines at least down to a core inner diameter of 20 mm.

The fins on the core are preferably designed to protrude slightly from one or both sides of the completed windings. If this is done they can be used to mount the core in a reliable and repeatable way.

Figure 21E:
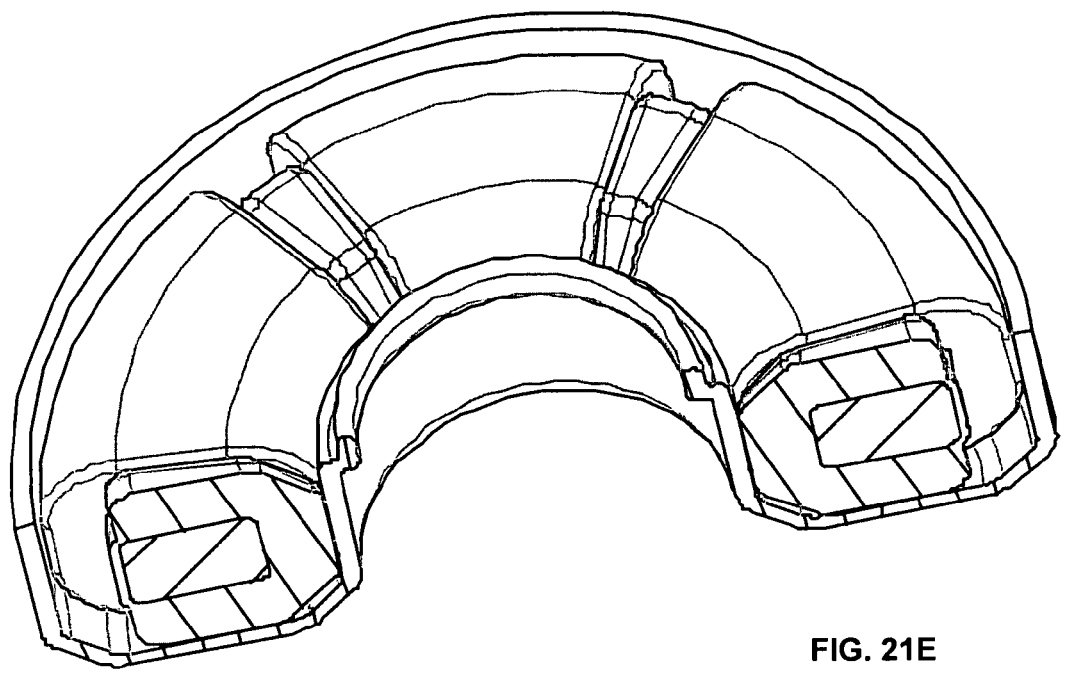

If the stator is to be mounted in a motor housing made from an electrically conductive material such as a metal, care must be taken that the coils do not come in contact with it. Separation can be maintained if the fins are extended considerably beyond the coils on one or both sides of the stator and then used to mount the stator in the motor casing. However a more reliable and compact method of mounting is to place the wound stator in a thin plastic shell as shown in FIG. 21E. The shell is bonded to the stator using epoxy adhesive or similar material.

Figure 21F:
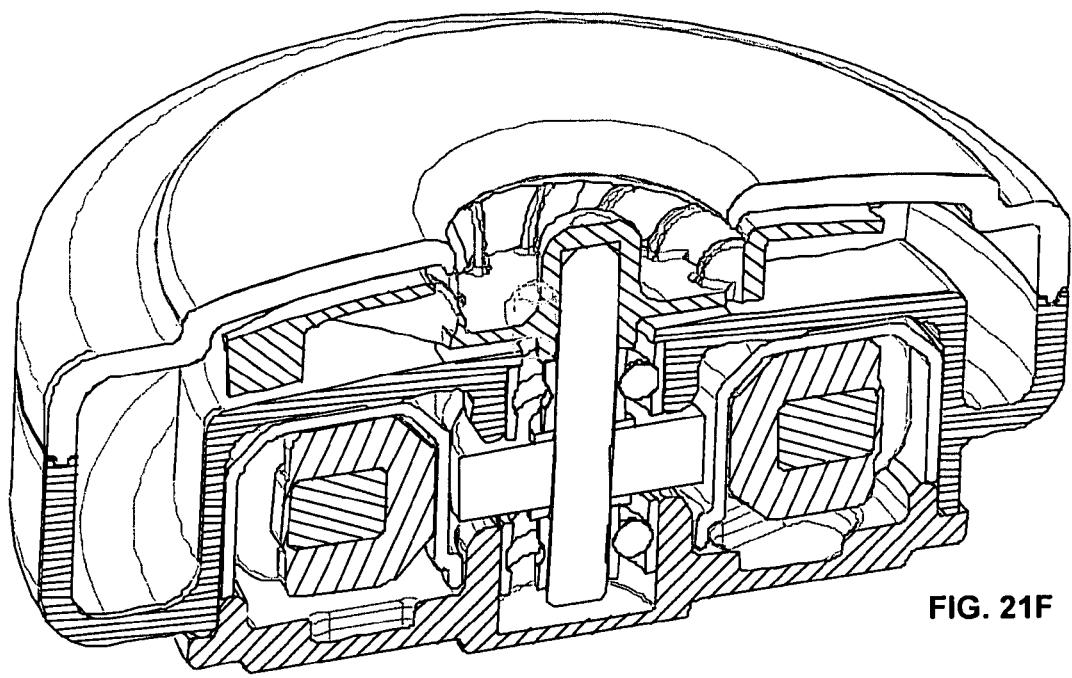

While the plastic shell takes up some space in the motor as shown in FIG. 21F, the size of the resulting stator assembly is extremely repeatable and it can be mounted tightly against even a metal motor casing. For this reason the design with a plastic shell is more suitable for high-volume production than the design that just relies on the fins on the core to separate the windings from the motor casing. In a high-volume application the design with a plastic shell actually produces a smaller motor than that without.

OTHER VARIATIONS AND MODIFICATIONS

It will be appreciated that a number of preferred embodiments have been hereinbefore described.

Numerous variations and modifications will become apparent to persons skilled in the art. For example, in FIG. 22 is shown how a 'visor' may be optionally attached to the device to provide protection to the eyes of the user. As shown, the visor 29 may be releasably attached to the attachment means 27.

All such variations and modifications which become apparent to persons skilled in the art should be considered to fall within the spirit and scope of this invention as hereinbefore described and as hereinafter claimed.

The invention claimed is:

1. A breathing apparatus, including:
   a mask adapted to substantially surround at least the mouth or nostrils of a user; and
   a neck component, adapted to substantially surround a rear portion of a neck of the user, further including a flow generator to receive unfiltered air from a surrounding environment, filter said unfiltered air, and provide filtered air to the mask, the neck component releasably engaged with the mask by at least one cooperating mating clip including an adjustment mechanism for moving and retaining the mask relative to the neck component;
   an inlet air channel arranged to convey air from the flow generator to the mask; and an air outlet, separate from the air inlet channel, arranged to convey air from the mask, wherein the mask and the neck component each include a portion defining part of the inlet air channel, and wherein the at least one cooperating mating clip releasably engages the portions, forming a seal therebetween.

2. A breathing apparatus as claimed in claim 1, wherein the inlet air channel is at least partly formed of an elastomeric material.

3. A breathing apparatus as claimed in claim 1, wherein the adjustment mechanism includes a ratchet mechanism and a release mechanism, and wherein the ratchet mechanism is decoupled upon activation of the release mechanism, thereby allowing the mask to move relative to the neck component.

4. A breathing apparatus as claimed in claim 1, further comprising electronic componentry configured to effect operation of the flow generator, wherein all the electronic componentry configured to effect operation of the flow generator is arranged within the neck component.

5. A breathing apparatus as claimed in claim 1, further including at least one of a cover, to decorate said mask, and a visor, to protect a face of the user.

6. A breathing apparatus as claimed in claim 1, further including a strap, adapted to be attached over a head of the user, to retain the mask in position.

7. A breathing apparatus as claimed in claim 1, further including at least one of a flow sensor and a pressure sensor, the flow sensor and pressure sensor configured to provide a feedback signal to the flow generator to adjust at least one of air flow and air pressure of the mask.

8. A breathing apparatus as claimed in claim 1, wherein the apparatus further includes a filter.

9. A breathing apparatus as claimed in claim 1, wherein the neck component further includes at least one padded portion arranged to abut the neck of the user.

10. The breathing apparatus as claimed in claim 6, wherein the inlet air channel and the air outlet open to the mask at opposite sides of the mask, so that the airflow is arranged to flow across the mouth or nostrils of the user.

11. A breathing apparatus as claimed in claim 1, further including an exhaled air filter arranged to filter air emitted from the air outlet.

12. A breathing apparatus as claimed in claim 11, wherein the exhaled air filter is integrally formed with an exhaust port.

13. The breathing apparatus as claimed in claim 11, wherein the air outlet extends between the mask and the neck component and includes an exhaust port arranged proximal to the neck component.

* * * * *